(12) United States Patent
Whitfill et al.

(10) Patent No.: US 11,773,154 B2
(45) Date of Patent: Oct. 3, 2023

(54) COMPOSITIONS AND METHODS FOR TREATMENT OF NETHERTON SYNDROME WITH LEKTI EXPRESSING RECOMBINANT MICROBES

(71) Applicant: Azitra Inc, Farmington, CT (US)

(72) Inventors: Travis Michael Whitfill, Dallas, TX (US); Azim Momin Munivar, New Haven, CT (US)

(73) Assignee: Azitra Inc, Branford, CT (US)

( * ) Notice: Subject to any disclaimer, the term of this patent is extended or adjusted under 35 U.S.C. 154(b) by 795 days.

(21) Appl. No.: 16/010,051

(22) Filed: Jun. 15, 2018

(65) Prior Publication Data

US 2019/0040116 A1 Feb. 7, 2019

Related U.S. Application Data

(60) Provisional application No. 62/521,050, filed on Jun. 16, 2017.

(51) Int. Cl.
| | | |
|---|---|---|
| *C07K 14/81* | (2006.01) | |
| *A61P 17/00* | (2006.01) | |
| *C12N 15/74* | (2006.01) | |
| *A61K 9/00* | (2006.01) | |
| *A61K 35/74* | (2015.01) | |

(52) U.S. Cl.
CPC ........ *C07K 14/8135* (2013.01); *A61K 9/0014* (2013.01); *A61K 35/74* (2013.01); *A61P 17/00* (2018.01); *C07K 14/81* (2013.01); *C07K 14/811* (2013.01); *C12N 15/74* (2013.01); *C12N 15/746* (2013.01)

(58) Field of Classification Search
CPC .... A61K 35/74; A61K 35/744; A61K 35/745; A61K 35/747; A61K 38/57; A61K 9/0014; A61P 17/00; C07K 14/81; C07K 14/811; C07K 14/8135; C12N 15/74; C12N 15/746
See application file for complete search history.

(56) References Cited

U.S. PATENT DOCUMENTS

| | | | |
|---|---|---|---|
| 9,737,592 B1 | 8/2017 | Bermudes et al. | |
| 10,702,558 B2 * | 7/2020 | Munivar | C12N 15/74 |
| 2003/0190637 A1 | 10/2003 | Hovnanian et al. | |
| 2014/0341881 A1 | 11/2014 | Deperthes et al. | |
| 2019/0040116 A1 † | 2/2019 | Whitfill | |

FOREIGN PATENT DOCUMENTS

| | | | |
|---|---|---|---|
| DE | 102009010942 A1 | 9/2010 | |
| WO | 2001/64747 A1 | 9/2001 | |
| WO | 2002/066513 A2 | 8/2002 | |
| WO | 2015/112081 A1 | 7/2015 | |
| WO | 2015/114144 A1 | 8/2015 | |
| WO | 2015/184134 A1 | 12/2015 | |
| WO | WO-2015184134 A1 * | 12/2015 | C12N 1/20 |

OTHER PUBLICATIONS

Bitoun E, et al "LEKTI proteolytic processing in human primary keratinocytes, tissue distribution and defective expression in Netherton syndrome" Hum Mol Genet. Oct. 1, 2003 (Epub Jul. 29, 2003),12(19), pp. 2417-2430; doi: 10.1093/hmg/ddg247. (Year: 2003).*
Stout et al., Recombinant filaggrin is internalized and processed to correct filaggrin deficiency. J Invest Dermatol. Feb. 2014;134(2):423-429.
International Search Report and Written Opinion for Application No. PCT/US2018/037850, dated Sep. 26, 2018, 14 pages.
Di et al., Ex-vivo gene therapy restores LEKTI activity and corrects the architecture of Netherton syndrome-derived skin grafts. Mol Ther. Feb. 2011;19(2):408-16.
Reutzmann et al., Recombinant production, purification and biochemical characterization of domain 6 of LEKTI: a temporary Kazal-type-related serine proteinase inhibitor. J Chromatogr B Analyt Technol Biomed Life Sci. Apr. 15, 2004;803(1):75-81.

\* cited by examiner
† cited by third party

*Primary Examiner* — Aaron J Kosar
(74) *Attorney, Agent, or Firm* — McCarter & English, LLP; Jonathan M. Sparks

(57) ABSTRACT

The present disclosure provides, inter alia, engineered microbes expressing recombinant LEKTI domains that are effective to treat or ameliorate the symptoms of Netherton Syndrome. In certain embodiments, compositions, methods, and kits are provided comprising LEKTI domain expressing microbes.

8 Claims, 10 Drawing Sheets

Specification includes a Sequence Listing.

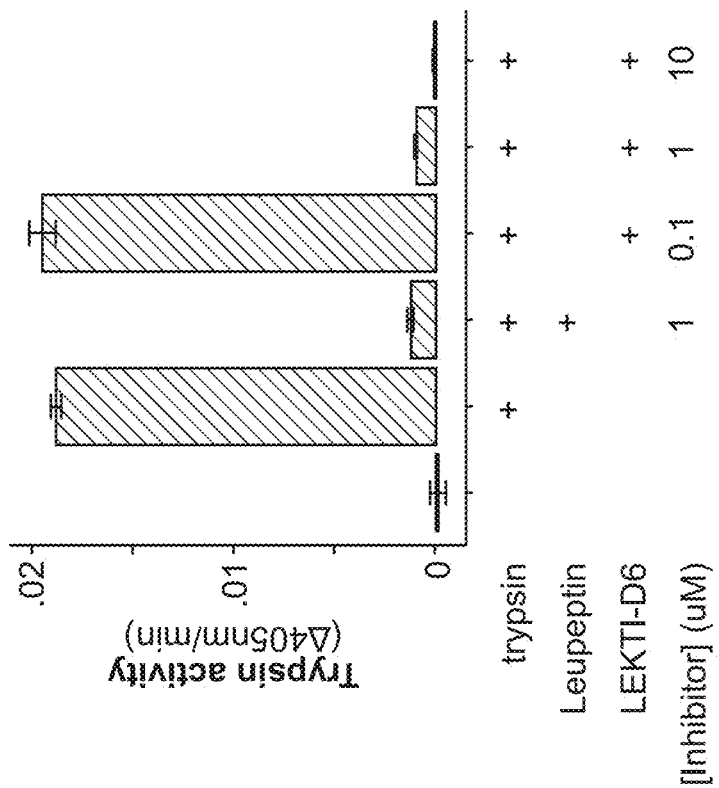
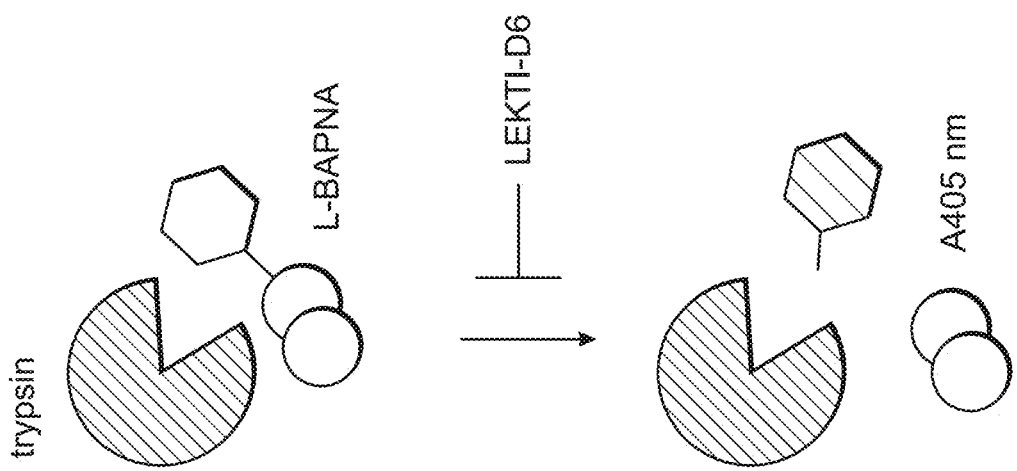

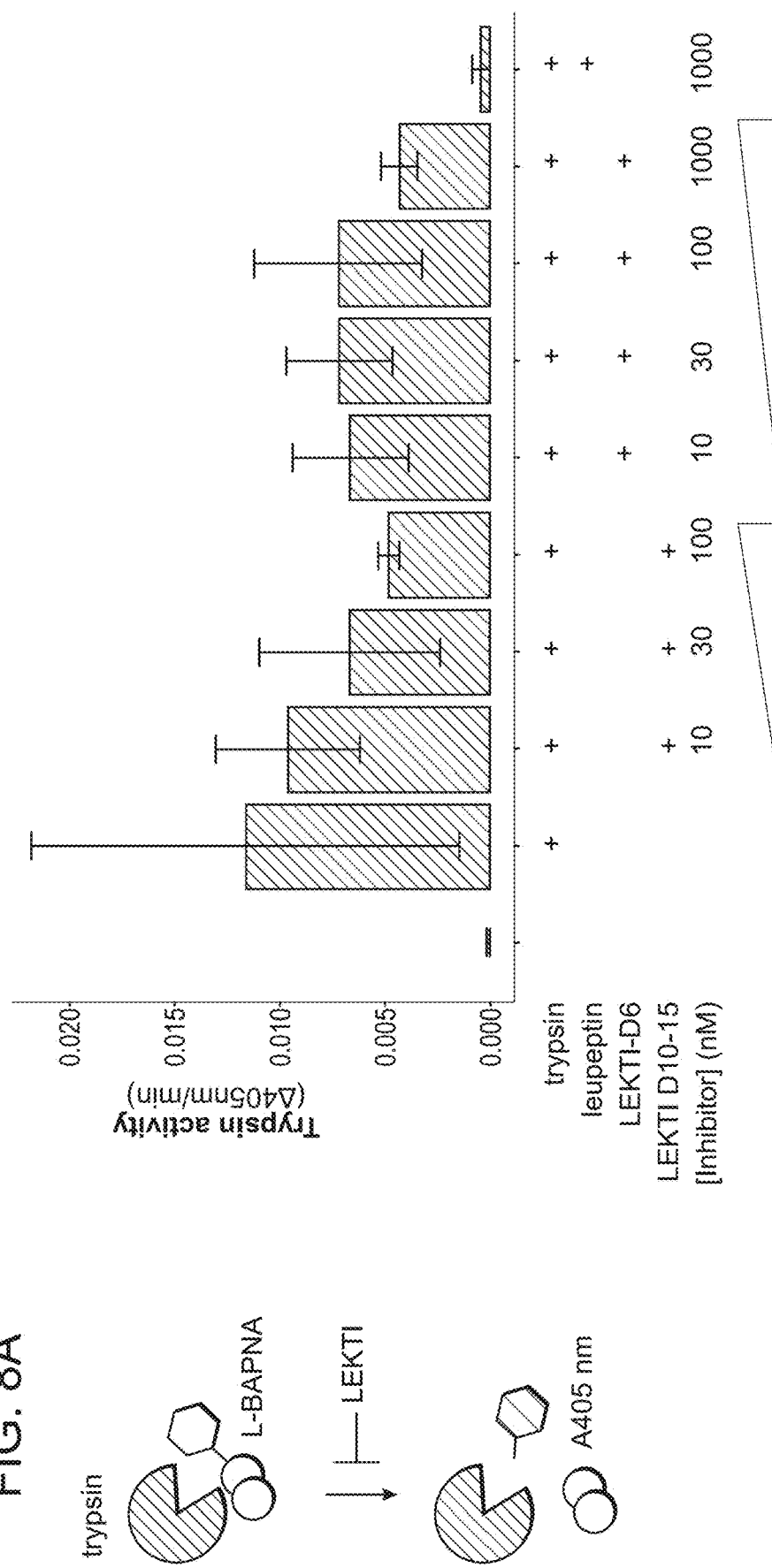

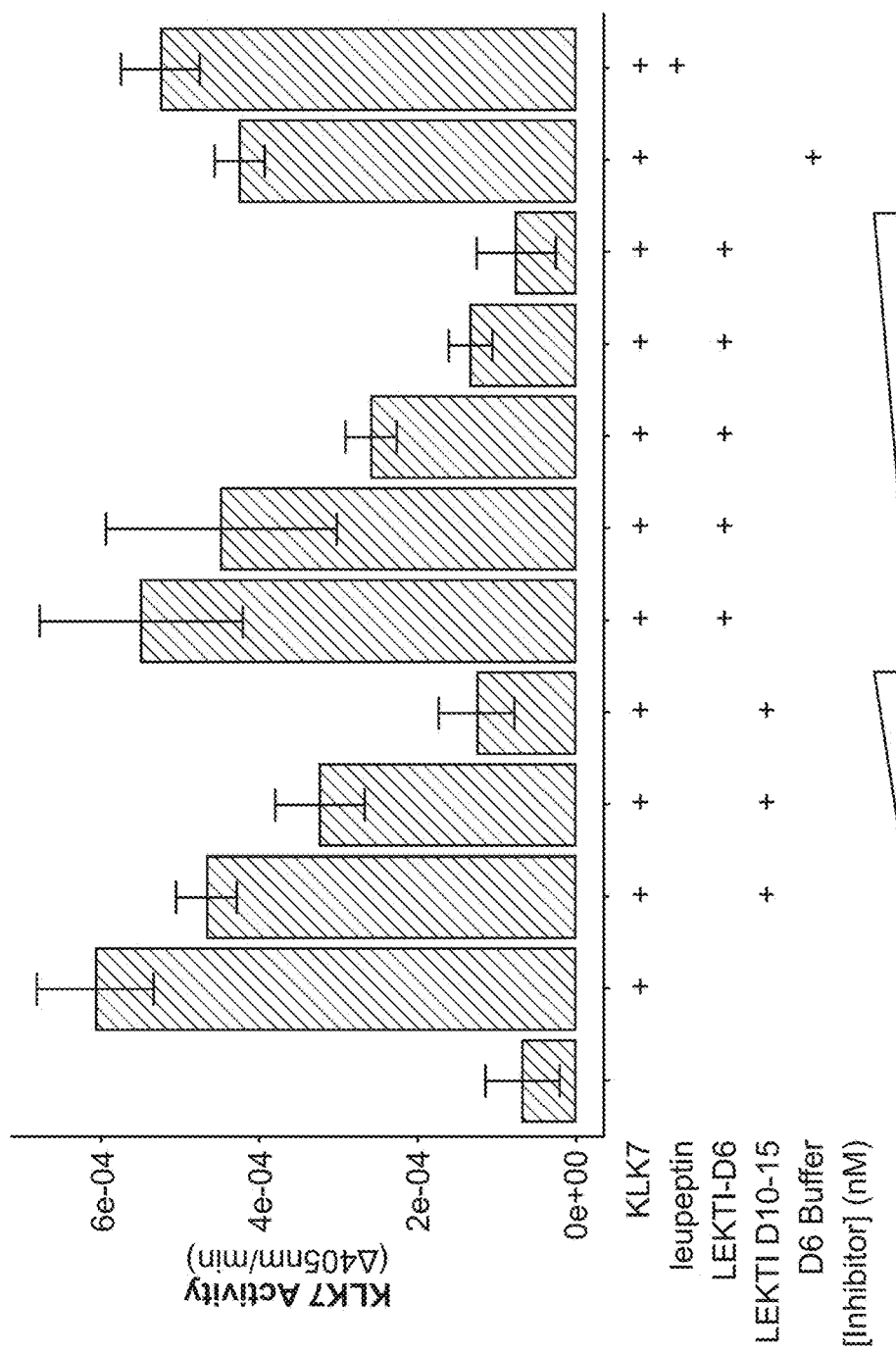
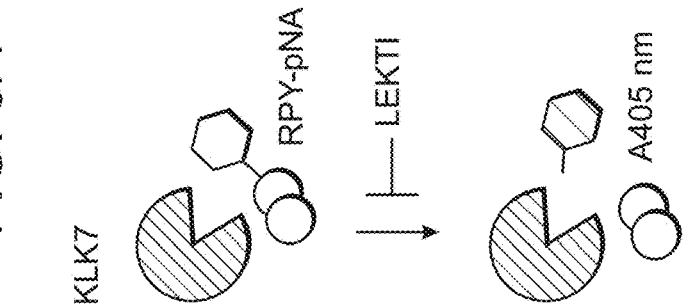
FIG. 9A
FIG. 9B

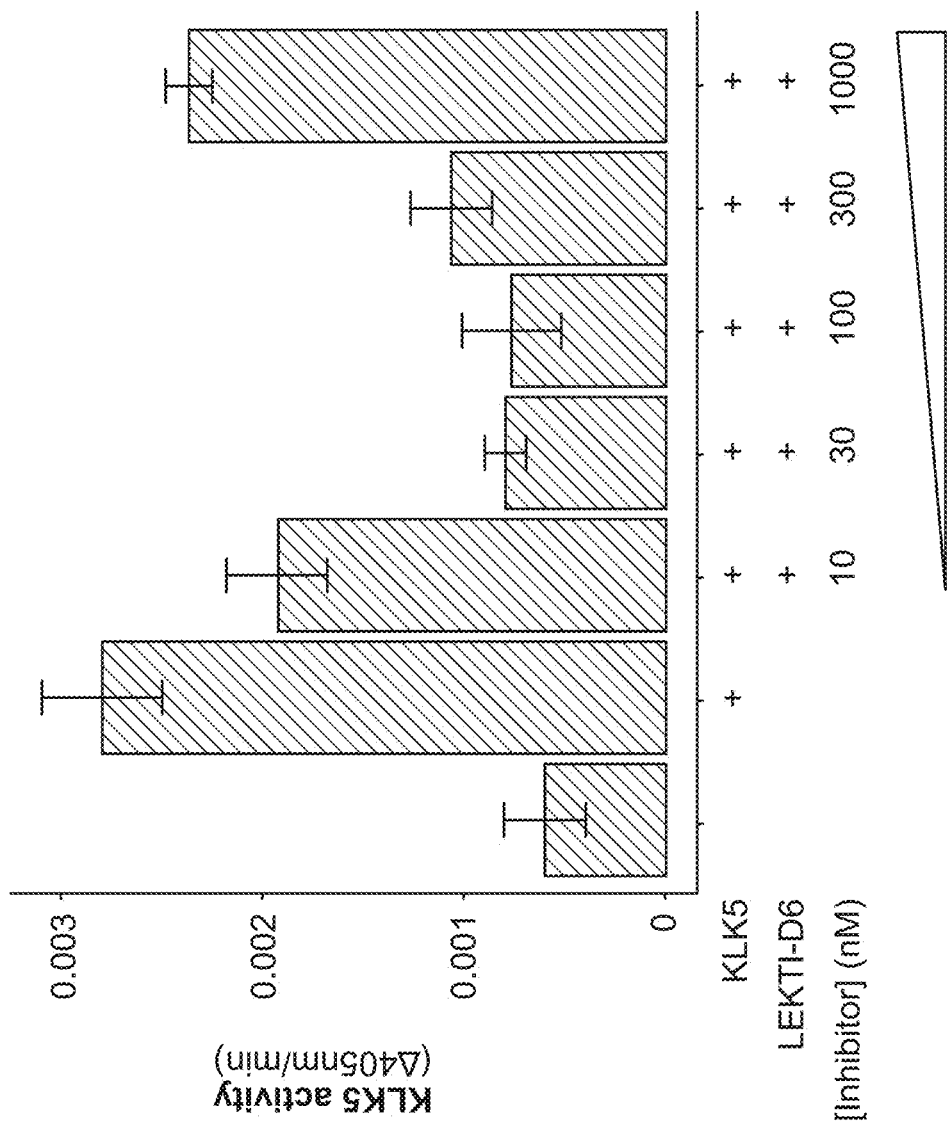
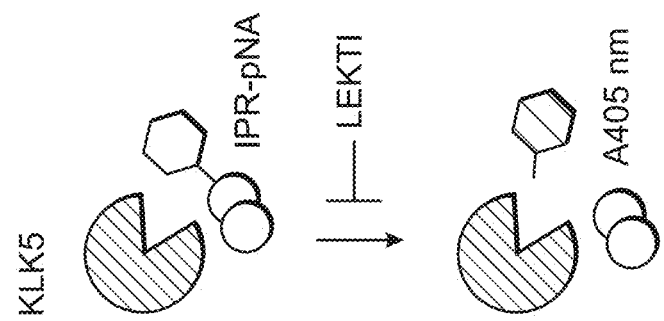

SEQUENCE LISTING

<160> NUMBER OF SEQ ID NOS: 125

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

```
<210> SEQ ID NO 9
<211> LENGTH: 25
<212> TYPE: PRT
<213> ORGANISM: Unknown
<220> FEATURE:
<223> OTHER INFORMATION: Description of Unknown:
      Secretion peptide

<400> SEQUENCE: 9

Met Lys Lys Leu Ala Phe Ala Ile Thr Ala Ala Ser Gly Ala Ala Ala
1               5                   10                  15

Val Leu Ser His His Asp Ala Glu Ala
            20                  25

<210> SEQ ID NO 10
<211> LENGTH: 30
<212> TYPE: PRT
<213> ORGANISM: Unknown
<220> FEATURE:
<223> OTHER INFORMATION: Description of Unknown:
      Secretion peptide

<400> SEQUENCE: 10

Trp Leu Asp Asn Arg Ala Phe Ser Lys Lys Phe Val Pro Val Val Met
1               5                   10                  15
```

```
Ala Thr Ser Val Ala Leu Phe Phe Leu Asn Leu Ala Phe Ala
            20                  25                  30
```

<210> SEQ ID NO 11
<211> LENGTH: 29
<212> TYPE: PRT
<213> ORGANISM: Unknown
<220> FEATURE:
<223> OTHER INFORMATION: Description of Unknown:
      Secretion peptide

<400> SEQUENCE: 11

```
Met Ala Lys Lys Phe Asn Tyr Lys Leu Pro Ser Met Val Ala Leu Thr
1               5                   10                  15

Leu Phe Gly Thr Ala Phe Thr Ala His Gln Ala Asn Ala
            20                  25
```

<210> SEQ ID NO 12
<211> LENGTH: 27
<212> TYPE: PRT
<213> ORGANISM: Unknown
<220> FEATURE:
<223> OTHER INFORMATION: Description of Unknown:
      Secretion peptide

<400> SEQUENCE: 12

```
Met Lys Lys Arg Phe Leu Ser Ile Cys Thr Met Thr Ile Ala Ala Leu
1               5                   10                  15

Ala Thr Thr Thr Met Val Asn Thr Ser Tyr Ala
            20                  25
```

<210> SEQ ID NO 13
<211> LENGTH: 30
<212> TYPE: PRT
<213> ORGANISM: Unknown
<220> FEATURE:
<223> OTHER INFORMATION: Description of Unknown:
      Secretion peptide

<400> SEQUENCE: 13

```
Asn Leu Lys Lys Gln Ser Lys Leu Ile Leu Ile Phe Ile Cys Ile Phe
1               5                   10                  15

Thr Phe Phe Ile Met Ile Ile Gln Ser Gln Phe Leu Met Gly
            20                  25                  30
```

<210> SEQ ID NO 14
<211> LENGTH: 26
<212> TYPE: PRT
<213> ORGANISM: Unknown
<220> FEATURE:
<223> OTHER INFORMATION: Description of Unknown:
      Secretion peptide

<400> SEQUENCE: 14

```
Met Lys Ile Phe Lys Leu Thr Ser Leu Thr Leu Ala Ala Leu Thr Leu
1               5                   10                  15

Ala Phe Pro Phe Ser His Val Ala Gln Ala
            20                  25
```

<210> SEQ ID NO 15
<211> LENGTH: 27
<212> TYPE: PRT
<213> ORGANISM: Unknown
<220> FEATURE:
<223> OTHER INFORMATION: Description of Unknown:

Secretion peptide

<400> SEQUENCE: 15

Met Lys Lys Thr Val Ile Ala Ser Thr Leu Ala Val Ser Leu Gly Ile
1               5                   10                  15

Ala Gly Tyr Gly Leu Ser Gly His Glu Ala His
            20                  25

<210> SEQ ID NO 16
<211> LENGTH: 27
<212> TYPE: PRT
<213> ORGANISM: Unknown
<220> FEATURE:
<223> OTHER INFORMATION: Description of Unknown:
      Secretion peptide

<400> SEQUENCE: 16

Met Lys Lys Asn Lys Phe Leu Val Tyr Leu Leu Ser Thr Ala Leu Ile
1               5                   10                  15

Thr Pro Thr Phe Ala Thr Gln Thr Ala Phe Ala
            20                  25

<210> SEQ ID NO 17
<211> LENGTH: 35
<212> TYPE: PRT
<213> ORGANISM: Unknown
<220> FEATURE:
<223> OTHER INFORMATION: Description of Unknown:
      Secretion peptide

<400> SEQUENCE: 17

Met Lys Thr Arg Gln Asn Lys Tyr Ser Ile Arg Lys Phe Ser Val Gly
1               5                   10                  15

Ala Ser Ser Ile Leu Ile Ala Ala Leu Leu Phe Met Gly Gly Gly Ser
            20                  25                  30

Ala Gln Ala
        35

<210> SEQ ID NO 18
<211> LENGTH: 37
<212> TYPE: PRT
<213> ORGANISM: Unknown
<220> FEATURE:
<223> OTHER INFORMATION: Description of Unknown:
      Secretion peptide

<400> SEQUENCE: 18

Met Lys Asn Asn Asn Glu Thr Arg Arg Phe Ser Ile Arg Lys Tyr Thr
1               5                   10                  15

Val Gly Val Val Ser Ile Ile Thr Gly Ile Thr Ile Phe Val Ser Gly
            20                  25                  30

Gln His Ala Gln Ala
        35

<210> SEQ ID NO 19
<211> LENGTH: 30
<212> TYPE: PRT
<213> ORGANISM: Unknown
<220> FEATURE:
<223> OTHER INFORMATION: Description of Unknown:
      Secretion peptide

<400> SEQUENCE: 19

Met Lys Lys Lys Leu Ser Tyr Met Ile Thr Ile Met Leu Ala Phe Thr

Leu Ser Leu Ala Leu Gly Leu Phe Phe Asn Ser Ala His Ala
            20                  25                  30

<210> SEQ ID NO 20
<211> LENGTH: 45
<212> TYPE: PRT
<213> ORGANISM: Staphylococcus epidermidis

<400> SEQUENCE: 20

Met Lys Lys Arg Arg Gln Gly Pro Ile Asn Lys Arg Val Asp Phe Leu
1               5                   10                  15

Ser Asn Lys Val Asn Lys Tyr Ser Ile Arg Lys Phe Thr Val Gly Thr
            20                  25                  30

Ala Ser Ile Leu Val Gly Ala Thr Leu Met Phe Gly Ala
        35                  40                  45

<210> SEQ ID NO 21
<211> LENGTH: 27
<212> TYPE: PRT
<213> ORGANISM: Staphylococcus epidermidis

<400> SEQUENCE: 21

Met Lys Lys Arg Phe Leu Ser Ile Cys Thr Met Thr Ile Ala Ala Leu
1               5                   10                  15

Ala Thr Thr Thr Met Val Asn Thr Ser Tyr Ala
            20                  25

<210> SEQ ID NO 22
<211> LENGTH: 29
<212> TYPE: PRT
<213> ORGANISM: Staphylococcus epidermidis

<400> SEQUENCE: 22

Met Ala Lys Lys Phe Asn Tyr Lys Leu Pro Ser Met Val Ala Leu Thr
1               5                   10                  15

Leu Phe Gly Thr Ala Phe Thr Ala His Gln Ala Asn Ala
            20                  25

<210> SEQ ID NO 23
<211> LENGTH: 50
<212> TYPE: PRT
<213> ORGANISM: Staphylococcus epidermidis

<400> SEQUENCE: 23

Met Ile Lys Lys Asn Asn Leu Leu Thr Lys Lys Pro Ile Ala Asn
1               5                   10                  15

Lys Ser Asn Lys Tyr Ala Ile Arg Lys Phe Thr Val Gly Thr Ala Ser
            20                  25                  30

Ile Val Ile Gly Ala Ala Leu Leu Phe Gly Leu Gly His Asn Glu Ala
        35                  40                  45

Lys Ala
    50

<210> SEQ ID NO 24
<211> LENGTH: 30
<212> TYPE: PRT
<213> ORGANISM: Staphylococcus epidermidis

<400> SEQUENCE: 24

Met Lys Pro Phe Lys Leu Ile Phe Ile Ser Ala Leu Met Ile Leu Ile

```
                1               5                  10                  15
Met Thr Asn Ala Thr Pro Ile Ser His Leu Asn Ala Gln Ala
            20                  25                  30

<210> SEQ ID NO 25
<211> LENGTH: 35
<212> TYPE: PRT
<213> ORGANISM: Staphylococcus epidermidis

<400> SEQUENCE: 25

Met Lys Thr Arg Gln Asn Lys Tyr Ser Ile Arg Lys Phe Ser Val Gly
1               5                   10                  15

Ala Ser Ser Ile Leu Ile Ala Ala Leu Leu Phe Met Gly Gly Gly Ser
            20                  25                  30

Ala Gln Ala
        35

<210> SEQ ID NO 26
<211> LENGTH: 23
<212> TYPE: PRT
<213> ORGANISM: Staphylococcus epidermidis

<400> SEQUENCE: 26

Met Asn Lys Phe Lys Phe Phe Ile Val Phe Leu Ile Leu Ser Leu Val
1               5                   10                  15

Phe Leu Gln Asn Glu Tyr Ala
            20

<210> SEQ ID NO 27
<211> LENGTH: 51
<212> TYPE: PRT
<213> ORGANISM: Staphylococcus epidermidis

<400> SEQUENCE: 27

Met Ile Asn Lys Lys Asn Asn Leu Leu Thr Lys Lys Lys Pro Ile Ala
1               5                   10                  15

Asn Lys Ser Asn Lys Tyr Ala Ile Arg Lys Phe Thr Val Gly Thr Ala
            20                  25                  30

Ser Ile Val Ile Gly Ala Thr Leu Leu Phe Gly Leu Gly His Asn Glu
        35                  40                  45

Ala Lys Ala
    50

<210> SEQ ID NO 28
<211> LENGTH: 26
<212> TYPE: PRT
<213> ORGANISM: Staphylococcus epidermidis

<400> SEQUENCE: 28

Met Lys Lys Ile Ala Thr Ala Thr Ile Ala Thr Ala Gly Ile Ala Thr
1               5                   10                  15

Phe Ala Phe Ala His His Asp Ala Gln Ala
            20                  25

<210> SEQ ID NO 29
<211> LENGTH: 28
<212> TYPE: PRT
<213> ORGANISM: Staphylococcus epidermidis

<400> SEQUENCE: 29

Met Lys Asn Phe Ser Lys Phe Ala Leu Thr Ser Ile Ala Ala Leu Thr
```

```
1               5                   10                  15
Val Ala Ser Pro Leu Val Asn Thr Glu Val Asp Ala
            20                  25
```

<210> SEQ ID NO 30
<211> LENGTH: 37
<212> TYPE: PRT
<213> ORGANISM: Staphylococcus epidermidis

<400> SEQUENCE: 30

```
Met Lys Asn Asn Glu Thr Arg Arg Phe Ser Ile Arg Lys Tyr Thr
1               5                   10                  15
Val Gly Val Val Ser Ile Ile Thr Gly Ile Thr Ile Phe Val Ser Gly
            20                  25                  30
Gln His Ala Gln Ala
        35
```

<210> SEQ ID NO 31
<211> LENGTH: 19
<212> TYPE: PRT
<213> ORGANISM: Staphylococcus epidermidis

<400> SEQUENCE: 31

```
Met Arg Tyr Leu Lys Arg Ile Thr Ile Tyr Ile Ser Leu Leu Ile Leu
1               5                   10                  15
Val Ser Gly
```

<210> SEQ ID NO 32
<211> LENGTH: 20
<212> TYPE: PRT
<213> ORGANISM: Staphylococcus epidermidis

<400> SEQUENCE: 32

```
Met Lys Leu Met Asn Lys Ile Ile Val Pro Val Thr Ala Ser Ala Leu
1               5                   10                  15
Leu Leu Gly Ala
            20
```

<210> SEQ ID NO 33
<211> LENGTH: 40
<212> TYPE: PRT
<213> ORGANISM: Staphylococcus epidermidis

<400> SEQUENCE: 33

```
Met Lys Lys Ile Asp Ser Trp Leu Thr Lys His Gly Leu Lys Asn Arg
1               5                   10                  15
Leu Thr Leu Val Val Ile Val Ile Phe Ile Ile Phe Leu Ile Leu Leu
            20                  25                  30
Phe Met Phe Val Asn Leu Ser Asp
        35                  40
```

<210> SEQ ID NO 34
<211> LENGTH: 19
<212> TYPE: PRT
<213> ORGANISM: Staphylococcus epidermidis

<400> SEQUENCE: 34

```
Met Lys Lys Lys Ala Leu Leu Pro Leu Phe Leu Gly Ile Met Ile Phe
1               5                   10                  15
Leu Ala Gly
```

<210> SEQ ID NO 35
<211> LENGTH: 28
<212> TYPE: PRT
<213> ORGANISM: Staphylococcus epidermidis

<400> SEQUENCE: 35

Met Lys Lys Thr Val Ile Ala Ser Thr Leu Ala Val Ser Leu Gly Ile
1               5                   10                  15

Ala Gly Tyr Gly Leu Ser Gly His Glu Ala His Ala
            20                  25

<210> SEQ ID NO 36
<211> LENGTH: 19
<212> TYPE: PRT
<213> ORGANISM: Staphylococcus epidermidis

<400> SEQUENCE: 36

Met Ser Lys Phe Lys Ser Leu Leu Leu Phe Gly Thr Leu Ile Leu
1               5                   10                  15

Leu Ser Gly

<210> SEQ ID NO 37
<211> LENGTH: 27
<212> TYPE: PRT
<213> ORGANISM: Staphylococcus epidermidis

<400> SEQUENCE: 37

Met Lys Lys Thr Leu Val Ala Ser Ser Leu Ala Ile Gly Leu Gly Val
1               5                   10                  15

Val Ala Gly Asn Ala Gly His Asp Ala His Ala
            20                  25

<210> SEQ ID NO 38
<211> LENGTH: 29
<212> TYPE: PRT
<213> ORGANISM: Staphylococcus epidermidis

<400> SEQUENCE: 38

Met Ala Lys Lys Phe Asn Tyr Lys Leu Pro Ser Met Val Ala Leu Thr
1               5                   10                  15

Leu Phe Gly Thr Ala Phe Thr Ala His Gln Ala Asn Ala
            20                  25

<210> SEQ ID NO 39
<211> LENGTH: 30
<212> TYPE: PRT
<213> ORGANISM: Staphylococcus epidermidis

<400> SEQUENCE: 39

Met Lys Lys Lys Leu Ser Tyr Met Ile Thr Ile Met Leu Ala Phe Thr
1               5                   10                  15

Leu Ser Leu Ala Leu Gly Leu Phe Phe Asn Ser Ala His Ala
            20                  25                  30

<210> SEQ ID NO 40
<211> LENGTH: 18
<212> TYPE: PRT
<213> ORGANISM: Staphylococcus epidermidis

<400> SEQUENCE: 40

Met His Lys Arg Leu Phe Ile Thr Leu Leu Gly Phe Ile Ile Leu Leu
1               5                   10                  15

Ala Gly

<210> SEQ ID NO 41
<211> LENGTH: 19
<212> TYPE: PRT
<213> ORGANISM: Staphylococcus epidermidis

<400> SEQUENCE: 41

Met Arg Tyr Leu Lys Arg Ile Thr Ile Tyr Ile Ser Leu Leu Ile Leu
1               5                   10                  15

Val Ser Gly

<210> SEQ ID NO 42
<211> LENGTH: 25
<212> TYPE: PRT
<213> ORGANISM: Staphylococcus epidermidis

<400> SEQUENCE: 42

Met Gln Lys Lys Tyr Ile Thr Ala Ile Ile Gly Thr Thr Ala Leu Ser
1               5                   10                  15

Ala Leu Ala Ser Thr His Ala Gln Ala
            20                  25

<210> SEQ ID NO 43
<211> LENGTH: 22
<212> TYPE: PRT
<213> ORGANISM: Staphylococcus epidermidis

<400> SEQUENCE: 43

Met Lys His Ser Ser Lys Ile Ile Val Phe Val Ser Phe Leu Ile Leu
1               5                   10                  15

Thr Ile Phe Ile Gly Gly
            20

<210> SEQ ID NO 44
<211> LENGTH: 20
<212> TYPE: PRT
<213> ORGANISM: Staphylococcus epidermidis

<400> SEQUENCE: 44

Met Lys Lys Trp Gln Leu Val Gly Thr Thr Val Leu Gly Ala Ser Val
1               5                   10                  15

Leu Leu Gly Ala
            20

<210> SEQ ID NO 45
<211> LENGTH: 52
<212> TYPE: PRT
<213> ORGANISM: Staphylococcus epidermidis

<400> SEQUENCE: 45

Met Gly Lys Arg Arg Gln Gly Pro Ile Asn Lys Val Asp Phe Leu
1               5                   10                  15

Pro Asn Lys Leu Asn Lys Tyr Ser Ile Arg Lys Phe Thr Val Gly Thr
            20                  25                  30

Ala Ser Ile Leu Leu Gly Ser Thr Leu Ile Phe Gly Ser Ser His
            35                  40                  45

Glu Ala Lys Ala
    50

-continued

```
<210> SEQ ID NO 46
<211> LENGTH: 26
<212> TYPE: PRT
<213> ORGANISM: Staphylococcus epidermidis

<400> SEQUENCE: 46
```

Met Lys Lys Ile Ala Thr Ala Thr Ile Ala Thr Ala Gly Ile Ala Thr
1               5                   10                  15

Phe Ala Phe Ala His His Asp Ala Gln Ala
            20                  25

```
<210> SEQ ID NO 47
<211> LENGTH: 45
<212> TYPE: PRT
<213> ORGANISM: Staphylococcus epidermidis

<400> SEQUENCE: 47
```

Met Lys Lys Arg Arg Gln Gly Pro Ile Asn Lys Arg Val Asp Phe Leu
1               5                   10                  15

Ser Asn Lys Val Asn Lys Tyr Ser Ile Arg Lys Phe Thr Val Gly Thr
            20                  25                  30

Ala Ser Ile Leu Val Gly Ala Thr Leu Met Phe Gly Ala
        35                  40                  45

```
<210> SEQ ID NO 48
<211> LENGTH: 27
<212> TYPE: PRT
<213> ORGANISM: Staphylococcus epidermidis

<400> SEQUENCE: 48
```

Met Lys Lys Arg Phe Leu Ser Ile Cys Thr Met Thr Ile Ala Ala Leu
1               5                   10                  15

Ala Thr Thr Thr Met Val Asn Thr Ser Tyr Ala
            20                  25

```
<210> SEQ ID NO 49
<211> LENGTH: 35
<212> TYPE: PRT
<213> ORGANISM: Staphylococcus epidermidis

<400> SEQUENCE: 49
```

Met Lys Thr Arg Gln Asn Lys Tyr Ser Ile Arg Lys Phe Ser Val Gly
1               5                   10                  15

Ala Ser Ser Ile Leu Ile Ala Ala Leu Leu Phe Met Gly Gly Gly Ser
            20                  25                  30

Ala Gln Ala
        35

```
<210> SEQ ID NO 50
<211> LENGTH: 28
<212> TYPE: PRT
<213> ORGANISM: Staphylococcus epidermidis

<400> SEQUENCE: 50
```

Met Lys Asn Phe Ser Lys Phe Ala Leu Thr Ser Ile Ala Ala Leu Thr
1               5                   10                  15

Val Ala Ser Pro Leu Val Asn Thr Glu Val Asp Ala
            20                  25

```
<210> SEQ ID NO 51
<211> LENGTH: 17
<212> TYPE: PRT
```

<213> ORGANISM: Staphylococcus epidermidis

<400> SEQUENCE: 51

Met Lys Lys Val Leu Ala Ser Ala Thr Ile Leu Ser Leu Met Leu Val
1               5                   10                  15

Gly

<210> SEQ ID NO 52
<211> LENGTH: 22
<212> TYPE: PRT
<213> ORGANISM: Staphylococcus epidermidis

<400> SEQUENCE: 52

Met Lys Tyr Tyr Gly Lys Cys Ile Ser Tyr Ile Ser Ile Leu Ile Leu
1               5                   10                  15

Thr Phe Phe Ile Gly Gly
            20

<210> SEQ ID NO 53
<211> LENGTH: 22
<212> TYPE: PRT
<213> ORGANISM: Staphylococcus epidermidis

<400> SEQUENCE: 53

Met Lys His Ser Ser Lys Ile Ile Val Phe Val Ser Phe Leu Ile Leu
1               5                   10                  15

Thr Ile Phe Ile Gly Gly
            20

<210> SEQ ID NO 54
<211> LENGTH: 30
<212> TYPE: PRT
<213> ORGANISM: Staphylococcus epidermidis

<400> SEQUENCE: 54

Met Lys Pro Phe Lys Leu Ile Phe Ile Ser Ala Leu Met Ile Leu Ile
1               5                   10                  15

Met Thr Asn Ala Thr Pro Ile Ser His Leu Asn Ala Gln Ala
            20                  25                  30

<210> SEQ ID NO 55
<211> LENGTH: 19
<212> TYPE: PRT
<213> ORGANISM: Staphylococcus epidermidis

<400> SEQUENCE: 55

Met Ser Lys Phe Lys Ser Leu Leu Leu Phe Gly Thr Leu Ile Leu
1               5                   10                  15

Leu Ser Gly

<210> SEQ ID NO 56
<211> LENGTH: 27
<212> TYPE: PRT
<213> ORGANISM: Staphylococcus epidermidis

<400> SEQUENCE: 56

Met Lys Lys Thr Leu Val Ala Ser Ser Leu Ala Ile Gly Leu Gly Val
1               5                   10                  15

Val Ala Gly Asn Ala Gly His Asp Ala His Ala
            20                  25

```
<210> SEQ ID NO 57
<211> LENGTH: 19
<212> TYPE: PRT
<213> ORGANISM: Staphylococcus epidermidis

<400> SEQUENCE: 57

Met His Tyr Leu Lys Lys Val Thr Ile Tyr Ile Ser Leu Leu Ile Leu
1               5                   10                  15

Val Ser Gly

<210> SEQ ID NO 58
<211> LENGTH: 25
<212> TYPE: PRT
<213> ORGANISM: Staphylococcus epidermidis

<400> SEQUENCE: 58

Met Gln Lys Lys Tyr Ile Thr Ala Ile Ile Gly Thr Thr Ala Leu Ser
1               5                   10                  15

Ala Leu Ala Ser Thr His Ala Gln Ala
            20                  25

<210> SEQ ID NO 59
<211> LENGTH: 22
<212> TYPE: PRT
<213> ORGANISM: Staphylococcus epidermidis

<400> SEQUENCE: 59

Met Lys His Ser Lys Lys Leu Leu Leu Cys Ile Ser Phe Leu Leu Ile
1               5                   10                  15

Thr Phe Phe Ile Gly Gly
            20

<210> SEQ ID NO 60
<211> LENGTH: 26
<212> TYPE: PRT
<213> ORGANISM: Staphylococcus epidermidis

<400> SEQUENCE: 60

Met Lys Lys Ile Ala Thr Ala Thr Ile Ala Thr Ala Gly Ile Ala Thr
1               5                   10                  15

Phe Ala Phe Ala His His Asp Ala Gln Ala
            20                  25

<210> SEQ ID NO 61
<211> LENGTH: 19
<212> TYPE: PRT
<213> ORGANISM: Staphylococcus epidermidis

<400> SEQUENCE: 61

Met Arg Tyr Leu Lys Lys Val Thr Ile Tyr Ile Ser Leu Leu Ile Leu
1               5                   10                  15

Val Ser Gly

<210> SEQ ID NO 62
<211> LENGTH: 27
<212> TYPE: PRT
<213> ORGANISM: Staphylococcus epidermidis

<400> SEQUENCE: 62

Met Lys Lys Arg Phe Leu Ser Ile Cys Thr Met Thr Ile Ala Ala Leu
1               5                   10                  15

Ala Thr Thr Thr Met Val Asn Thr Ser Tyr Ala
```

```
<210> SEQ ID NO 63
<211> LENGTH: 20
<212> TYPE: PRT
<213> ORGANISM: Staphylococcus epidermidis

<400> SEQUENCE: 63

Met Lys Lys Trp Gln Leu Val Gly Thr Thr Val Leu Gly Ala Ser Val
1               5                   10                  15

Leu Leu Gly Ala
            20

<210> SEQ ID NO 64
<211> LENGTH: 29
<212> TYPE: PRT
<213> ORGANISM: Staphylococcus epidermidis

<400> SEQUENCE: 64

Met Ala Lys Lys Phe Asn Tyr Lys Leu Pro Ser Met Val Ala Leu Thr
1               5                   10                  15

Leu Phe Gly Thr Ala Phe Thr Ala His Gln Ala Asn Ala
            20                  25

<210> SEQ ID NO 65
<211> LENGTH: 30
<212> TYPE: PRT
<213> ORGANISM: Staphylococcus epidermidis

<400> SEQUENCE: 65

Met Lys Lys Lys Leu Ser Tyr Met Ile Thr Ile Met Leu Ala Phe Thr
1               5                   10                  15

Leu Ser Leu Ala Leu Gly Leu Phe Phe Asn Ser Ala His Ala
            20                  25                  30

<210> SEQ ID NO 66
<211> LENGTH: 18
<212> TYPE: PRT
<213> ORGANISM: Staphylococcus epidermidis

<400> SEQUENCE: 66

Met His Lys Arg Leu Phe Ile Thr Leu Leu Gly Phe Ile Ile Leu Leu
1               5                   10                  15

Ala Gly

<210> SEQ ID NO 67
<211> LENGTH: 22
<212> TYPE: PRT
<213> ORGANISM: Staphylococcus epidermidis

<400> SEQUENCE: 67

Met Arg Tyr Leu Lys Lys Val Thr Ile Tyr Ile Ser Leu Leu Ile Leu
1               5                   10                  15

Thr Ile Phe Ile Gly Gly
            20

<210> SEQ ID NO 68
<211> LENGTH: 17
<212> TYPE: PRT
<213> ORGANISM: Staphylococcus epidermidis

<400> SEQUENCE: 68
```

Met Lys Lys Val Leu Ala Ser Ala Thr Ile Leu Ser Leu Met Leu Val
1               5                   10                  15

Gly

<210> SEQ ID NO 69
<211> LENGTH: 22
<212> TYPE: PRT
<213> ORGANISM: Staphylococcus epidermidis

<400> SEQUENCE: 69

Met Lys His Ser Lys Lys Leu Leu Leu Cys Ile Ser Phe Leu Leu Ile
1               5                   10                  15

Thr Val Phe Ile Ser Gly
            20

<210> SEQ ID NO 70
<211> LENGTH: 22
<212> TYPE: PRT
<213> ORGANISM: Staphylococcus epidermidis

<400> SEQUENCE: 70

Met Lys His Ser Lys Lys Leu Leu Leu Cys Ile Ser Phe Leu Leu Ile
1               5                   10                  15

Thr Phe Phe Ile Ser Gly
            20

<210> SEQ ID NO 71
<211> LENGTH: 28
<212> TYPE: PRT
<213> ORGANISM: Staphylococcus epidermidis

<400> SEQUENCE: 71

Met Lys Lys Thr Val Ile Ala Ser Thr Leu Ala Val Ser Leu Gly Ile
1               5                   10                  15

Ala Gly Tyr Gly Leu Ser Gly His Glu Ala His Ala
            20                  25

<210> SEQ ID NO 72
<211> LENGTH: 22
<212> TYPE: PRT
<213> ORGANISM: Staphylococcus epidermidis

<400> SEQUENCE: 72

Met Lys His Ser Lys Lys Leu Leu Leu Cys Ile Ser Phe Leu Leu Ile
1               5                   10                  15

Thr Ile Phe Ile Ser Gly
            20

<210> SEQ ID NO 73
<211> LENGTH: 40
<212> TYPE: PRT
<213> ORGANISM: Staphylococcus epidermidis

<400> SEQUENCE: 73

Met Lys Lys Ile Asp Ser Trp Leu Thr Lys His Gly Leu Lys Asn Arg
1               5                   10                  15

Leu Thr Leu Val Val Ile Val Ile Phe Ile Ile Phe Leu Ile Leu Leu
            20                  25                  30

Phe Met Phe Val Asn Leu Ser Asp
        35                  40

<210> SEQ ID NO 74
<211> LENGTH: 19
<212> TYPE: PRT
<213> ORGANISM: Staphylococcus epidermidis

<400> SEQUENCE: 74

Met Lys Lys Lys Ala Leu Leu Pro Leu Phe Leu Gly Ile Met Ile Phe
1               5                   10                  15

Leu Ala Gly

<210> SEQ ID NO 75
<211> LENGTH: 20
<212> TYPE: PRT
<213> ORGANISM: Staphylococcus epidermidis

<400> SEQUENCE: 75

Met Lys Leu Met Asn Lys Ile Ile Val Pro Val Thr Ala Ser Ala Leu
1               5                   10                  15

Leu Leu Gly Ala
            20

<210> SEQ ID NO 76
<211> LENGTH: 35
<212> TYPE: PRT
<213> ORGANISM: Staphylococcus epidermidis

<400> SEQUENCE: 76

Met Lys Thr Arg Gln Asn Lys Tyr Ser Ile Arg Lys Phe Ser Val Gly
1               5                   10                  15

Ala Ser Ser Ile Leu Ile Ala Ala Leu Leu Phe Met Gly Gly Gly Ser
            20                  25                  30

Ala Gln Ala
        35

<210> SEQ ID NO 77
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 77

Gly Arg Lys Lys Arg Arg Gln Arg Arg Arg Pro Pro Gln
1               5                   10

<210> SEQ ID NO 78
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 78

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 79
<211> LENGTH: 18
<212> TYPE: PRT
<213> ORGANISM: Unknown

```
<220> FEATURE:
<223> OTHER INFORMATION: Description of Unknown:
      Cell penetrating peptide

<400> SEQUENCE: 79

Lys Leu Ala Leu Lys Leu Ala Leu Lys Ala Leu Lys Ala Ala Leu Lys
1               5                   10                  15

Leu Ala

<210> SEQ ID NO 80
<211> LENGTH: 30
<212> TYPE: PRT
<213> ORGANISM: Unknown
<220> FEATURE:
<223> OTHER INFORMATION: Description of Unknown:
      Cell penetrating peptide

<400> SEQUENCE: 80

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 81
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 81

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 82
<211> LENGTH: 9
<212> TYPE: PRT
<213> ORGANISM: Unknown
<220> FEATURE:
<223> OTHER INFORMATION: Description of Unknown:
      Cell penetrating peptide

<400> SEQUENCE: 82

Arg Arg Arg Arg Arg Arg Arg Arg
1               5

<210> SEQ ID NO 83
<211> LENGTH: 24
<212> TYPE: PRT
<213> ORGANISM: Unknown
<220> FEATURE:
<223> OTHER INFORMATION: Description of Unknown:
      Cell penetrating peptide

<400> SEQUENCE: 83

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 84
<211> LENGTH: 15
```

```
<212> TYPE: PRT
<213> ORGANISM: Unknown
<220> FEATURE:
<223> OTHER INFORMATION: Description of Unknown:
      Cell penetrating peptide

<400> SEQUENCE: 84

Arg Gln Ile Lys Trp Phe Gln Asn Arg Arg Met Lys Trp Lys Lys
1               5                   10                  15

<210> SEQ ID NO 85
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 85

Tyr Gly Arg Lys Lys Arg Arg Gln Arg Arg
1               5                   10

<210> SEQ ID NO 86
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 86

Arg Gly Gly Arg Leu Ser Tyr Ser Arg Arg Arg Phe Ser Thr Ser Thr
1               5                   10                  15

Gly Arg

<210> SEQ ID NO 87
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 87

Arg Arg Leu Ser Tyr Ser Arg Arg Arg Phe
1               5                   10

<210> SEQ ID NO 88
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 88

Pro Ile Arg Arg Arg Lys Lys Leu Arg Arg Leu Lys
1               5                   10

<210> SEQ ID NO 89
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 89
```

```
Arg Arg Gln Arg Arg Thr Ser Lys Leu Met Lys Arg
1               5                   10
```

```
<210> SEQ ID NO 90
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 90
```

```
Arg Arg Arg Arg Asn Arg Thr Arg Arg Asn Arg Arg Arg Val Arg
1               5                   10                  15
```

```
<210> SEQ ID NO 91
<211> LENGTH: 19
<212> TYPE: PRT
<213> ORGANISM: Unknown
<220> FEATURE:
<223> OTHER INFORMATION: Description of Unknown:
      Cell penetrating peptide

<400> SEQUENCE: 91
```

```
Lys Met Thr Arg Ala Gln Arg Arg Ala Ala Ala Arg Arg Asn Arg Trp
1               5                   10                  15

Thr Ala Arg
```

```
<210> SEQ ID NO 92
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 92
```

```
Thr Arg Arg Gln Arg Thr Arg Arg Ala Arg Arg Asn Arg
1               5                   10
```

```
<210> SEQ ID NO 93
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 93
```

```
Gly Arg Lys Lys Arg Arg Gln Arg Arg Arg Pro Pro Gln
1               5                   10
```

```
<210> SEQ ID NO 94
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 94
```

```
Gly Arg Arg Arg Arg Arg Arg Arg Arg Arg Pro Pro Gln
1               5                   10
```

```
<210> SEQ ID NO 95
<211> LENGTH: 27
```

```
<212> TYPE: PRT
<213> ORGANISM: Unknown
<220> FEATURE:
<223> OTHER INFORMATION: Description of Unknown:
      Cell penetrating peptide

<400> SEQUENCE: 95

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 96
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 96

Lys Leu Ala Leu Lys Leu Ala Leu Lys Leu Ala Leu Ala Leu Lys Leu
1               5                   10                  15

Ala

<210> SEQ ID NO 97
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 97

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 98
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 98

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 99
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 99

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
```

20                  25

<210> SEQ ID NO 100
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 100

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 101
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 101

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 102
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 102

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 103
<211> LENGTH: 1064
<212> TYPE: PRT
<213> ORGANISM: Unknown
<220> FEATURE:
<223> OTHER INFORMATION: Description of Unknown:
      sequence

<400> SEQUENCE: 103

Met Lys Ile Ala Thr Val Ser Val Leu Leu Pro Leu Ala Leu Cys Leu
1               5                   10                  15

Ile Gln Asp Ala Ala Ser Lys Asn Glu Asp Gln Glu Met Cys His Glu
            20                  25                  30

Phe Gln Ala Phe Met Lys Asn Gly Lys Leu Phe Cys Pro Gln Asp Lys
        35                  40                  45

Lys Phe Phe Gln Ser Leu Asp Gly Ile Met Phe Ile Asn Lys Cys Ala
    50                  55                  60

Thr Cys Lys Met Ile Leu Glu Lys Glu Ala Lys Ser Gln Lys Arg Ala
65                  70                  75                  80

```
Arg His Leu Ala Arg Ala Pro Lys Ala Thr Ala Pro Thr Glu Leu Asn
                85                  90                  95

Cys Asp Asp Phe Lys Lys Gly Glu Arg Asp Gly Asp Phe Ile Cys Pro
            100                 105                 110

Asp Tyr Tyr Glu Ala Val Cys Gly Thr Asp Gly Lys Thr Tyr Asp Asn
        115                 120                 125

Arg Cys Ala Leu Cys Ala Glu Asn Ala Lys Thr Gly Ser Gln Ile Gly
    130                 135                 140

Val Lys Ser Glu Gly Glu Cys Lys Ser Ser Asn Pro Glu Gln Asp Val
145                 150                 155                 160

Cys Ser Ala Phe Arg Pro Phe Val Arg Asp Gly Arg Leu Gly Cys Thr
                165                 170                 175

Arg Glu Asn Asp Pro Val Leu Gly Pro Asp Gly Lys Thr His Gly Asn
            180                 185                 190

Lys Cys Ala Met Cys Ala Glu Leu Phe Leu Lys Glu Ala Glu Asn Ala
        195                 200                 205

Lys Arg Glu Gly Glu Thr Arg Ile Arg Arg Asn Ala Glu Lys Asp Phe
    210                 215                 220

Cys Lys Glu Tyr Glu Lys Gln Val Arg Asn Gly Arg Leu Phe Cys Thr
225                 230                 235                 240

Arg Glu Ser Asp Pro Val Arg Gly Pro Asp Gly Arg Met His Gly Asn
                245                 250                 255

Lys Cys Ala Leu Cys Ala Glu Ile Phe Lys Gln Arg Phe Ser Glu Glu
            260                 265                 270

Asn Ser Lys Thr Asp Gln Asn Leu Gly Lys Ala Glu Glu Lys Thr Lys
        275                 280                 285

Val Lys Arg Glu Ile Val Lys Leu Cys Ser Gln Tyr Gln Asn Gln Ala
    290                 295                 300

Lys Asn Gly Ile Leu Phe Cys Thr Arg Glu Asn Asp Pro Ile Arg Gly
305                 310                 315                 320

Pro Asp Gly Lys Met His Gly Asn Leu Cys Ser Met Cys Gln Ala Tyr
                325                 330                 335

Phe Gln Ala Glu Asn Glu Glu Lys Lys Lys Ala Glu Ala Arg Ala Arg
            340                 345                 350

Asn Lys Arg Glu Ser Gly Lys Ala Thr Ser Tyr Ala Glu Leu Cys Ser
        355                 360                 365

Glu Tyr Arg Lys Leu Val Arg Asn Gly Lys Leu Ala Cys Thr Arg Glu
    370                 375                 380

Asn Asp Pro Ile Gln Gly Pro Asp Gly Lys Val His Gly Asn Thr Cys
385                 390                 395                 400

Ser Met Cys Glu Val Phe Phe Gln Ala Glu Glu Glu Lys Lys Lys
                405                 410                 415

Lys Glu Gly Lys Ser Arg Asn Lys Arg Gln Ser Lys Ser Thr Ala Ser
            420                 425                 430

Phe Glu Glu Leu Cys Ser Glu Tyr Arg Lys Ser Arg Lys Asn Gly Arg
        435                 440                 445

Leu Phe Cys Thr Arg Glu Asn Asp Pro Ile Gln Gly Pro Asp Gly Lys
    450                 455                 460

Met His Gly Asn Thr Cys Ser Met Cys Glu Ala Phe Phe Gln Gln Glu
465                 470                 475                 480

Glu Arg Ala Arg Ala Lys Ala Lys Arg Glu Ala Ala Lys Glu Ile Cys
                485                 490                 495

Ser Glu Phe Arg Asp Gln Val Arg Asn Gly Thr Leu Ile Cys Thr Arg
```

```
                500                 505                 510
Glu His Asn Pro Val Arg Gly Pro Asp Gly Lys Met His Gly Asn Lys
        515                 520                 525

Cys Ala Met Cys Ala Ser Val Phe Lys Leu Glu Glu Glu Lys Lys
        530                 535                 540

Asn Asp Lys Glu Glu Lys Gly Lys Val Glu Ala Glu Lys Val Lys Arg
545                 550                 555                 560

Glu Ala Val Gln Glu Leu Cys Ser Glu Tyr Arg His Tyr Val Arg Asn
                565                 570                 575

Gly Arg Leu Pro Cys Thr Arg Glu Asn Asp Pro Ile Glu Gly Leu Asp
            580                 585                 590

Gly Lys Ile His Gly Asn Thr Cys Ser Met Cys Glu Ala Phe Phe Gln
        595                 600                 605

Gln Glu Ala Lys Glu Lys Glu Arg Ala Glu Pro Arg Ala Lys Val Lys
        610                 615                 620

Arg Glu Ala Glu Lys Glu Thr Cys Asp Glu Phe Arg Arg Leu Leu Gln
625                 630                 635                 640

Asn Gly Lys Leu Phe Cys Thr Arg Glu Asn Asp Pro Val Arg Gly Pro
                645                 650                 655

Asp Gly Lys Thr His Gly Asn Lys Cys Ala Met Cys Lys Ala Val Phe
            660                 665                 670

Gln Lys Glu Asn Glu Glu Arg Lys Arg Lys Glu Glu Glu Asp Gln Arg
        675                 680                 685

Asn Ala Ala Gly His Gly Ser Ser Gly Gly Gly Gly Asn Thr Gln
        690                 695                 700

Asp Glu Cys Ala Glu Tyr Arg Glu Gln Met Lys Asn Gly Arg Leu Ser
705                 710                 715                 720

Cys Thr Arg Glu Ser Asp Pro Val Arg Asp Ala Asp Gly Lys Ser Tyr
                725                 730                 735

Asn Asn Gln Cys Thr Met Cys Lys Ala Lys Leu Glu Arg Glu Ala Glu
            740                 745                 750

Arg Lys Asn Glu Tyr Ser Arg Ser Arg Ser Asn Gly Thr Gly Ser Glu
        755                 760                 765

Ser Gly Lys Asp Thr Cys Asp Glu Phe Arg Ser Gln Met Lys Asn Gly
        770                 775                 780

Lys Leu Ile Cys Thr Arg Glu Ser Asp Pro Val Arg Gly Pro Asp Gly
785                 790                 795                 800

Lys Thr His Gly Asn Lys Cys Thr Met Cys Lys Glu Lys Leu Glu Arg
                805                 810                 815

Glu Ala Ala Glu Lys Lys Lys Glu Asp Glu Asp Arg Ser Asn Thr
            820                 825                 830

Gly Glu Arg Ser Asn Thr Gly Glu Arg Ser Asn Asp Lys Glu Asp Leu
        835                 840                 845

Cys Arg Glu Phe Arg Ser Met Gln Arg Asn Gly Lys Leu Ile Cys Thr
        850                 855                 860

Arg Glu Asn Asn Pro Val Arg Gly Pro Tyr Gly Lys Met His Ile Asn
865                 870                 875                 880

Lys Cys Ala Met Cys Gln Ser Ile Phe Asp Arg Glu Ala Asn Glu Arg
                885                 890                 895

Lys Lys Lys Asp Glu Glu Lys Ser Ser Ser Lys Pro Ser Asn Asn Ala
            900                 905                 910

Lys Asp Glu Cys Ser Glu Phe Arg Asn Tyr Ile Arg Asn Asn Glu Leu
        915                 920                 925
```

Ile Cys Pro Arg Glu Asn Asp Pro Val His Gly Ala Asp Gly Lys Phe
930                 935                 940

Tyr Thr Asn Lys Cys Tyr Met Cys Arg Ala Val Phe Leu Thr Glu Ala
945                 950                 955                 960

Leu Glu Arg Ala Lys Leu Gln Glu Lys Pro Ser His Val Arg Ala Ser
            965                 970                 975

Gln Glu Glu Asp Ser Pro Asp Ser Phe Ser Ser Leu Asp Ser Glu Met
            980                 985                 990

Cys Lys Asp Tyr Arg Val Leu Pro Arg Ile Gly Tyr Leu Cys Pro Lys
            995                 1000                1005

Asp Leu Lys Pro Val Cys Gly Asp Asp Gly Gln Thr Tyr Asn Asn
    1010                1015                1020

Pro Cys Met Leu Cys His Glu Asn Leu Ile Arg Gln Thr Asn Thr
    1025                1030                1035

His Ile Arg Ser Thr Gly Lys Cys Glu Glu Ser Ser Thr Pro Gly
    1040                1045                1050

Thr Thr Ala Ala Ser Met Pro Pro Ser Asp Glu
    1055                1060

<210> SEQ ID NO 104
<211> LENGTH: 55
<212> TYPE: PRT
<213> ORGANISM: Unknown
<220> FEATURE:
<223> OTHER INFORMATION: Description of Unknown:
      sequence

<400> SEQUENCE: 104

Lys Asn Glu Asp Gln Glu Met Cys His Glu Phe Gln Ala Phe Met Lys
1               5                   10                  15

Asn Gly Lys Leu Phe Cys Pro Gln Asp Lys Lys Phe Phe Gln Ser Leu
            20                  25                  30

Asp Gly Ile Met Phe Ile Asn Lys Cys Ala Thr Cys Lys Met Ile Leu
        35                  40                  45

Glu Lys Glu Ala Lys Ser Gln
    50                  55

<210> SEQ ID NO 105
<211> LENGTH: 63
<212> TYPE: PRT
<213> ORGANISM: Unknown
<220> FEATURE:
<223> OTHER INFORMATION: Description of Unknown:
      sequence

<400> SEQUENCE: 105

Ala Pro Thr Glu Leu Asn Cys Asp Phe Lys Lys Gly Glu Arg Asp
1               5                   10                  15

Gly Asp Phe Ile Cys Pro Asp Tyr Tyr Glu Ala Val Cys Gly Thr Asp
            20                  25                  30

Gly Lys Thr Tyr Asp Asn Arg Cys Ala Leu Cys Ala Glu Asn Ala Lys
        35                  40                  45

Thr Gly Ser Gln Ile Gly Val Lys Ser Glu Gly Glu Cys Lys Ser
    50                  55                  60

<210> SEQ ID NO 106
<211> LENGTH: 62
<212> TYPE: PRT
<213> ORGANISM: Unknown

```
<220> FEATURE:
<223> OTHER INFORMATION: Description of Unknown:
      sequence

<400> SEQUENCE: 106

Asn Pro Glu Gln Asp Val Cys Ser Ala Phe Arg Pro Phe Val Arg Asp
1               5                  10                  15

Gly Arg Leu Gly Cys Thr Arg Glu Asn Asp Pro Val Leu Gly Pro Asp
            20                  25                  30

Gly Lys Thr His Gly Asn Lys Cys Ala Met Cys Ala Glu Leu Phe Leu
        35                  40                  45

Lys Glu Ala Glu Asn Ala Lys Arg Gly Glu Thr Arg Ile
    50                  55                  60

<210> SEQ ID NO 107
<211> LENGTH: 67
<212> TYPE: PRT
<213> ORGANISM: Unknown
<220> FEATURE:
<223> OTHER INFORMATION: Description of Unknown:
      sequence

<400> SEQUENCE: 107

Asn Ala Glu Lys Asp Phe Cys Lys Glu Tyr Glu Lys Gln Val Arg Asn
1               5                  10                  15

Gly Arg Leu Phe Cys Thr Arg Glu Ser Asp Pro Val Arg Gly Pro Asp
            20                  25                  30

Gly Arg Met His Gly Asn Lys Cys Ala Leu Cys Ala Glu Ile Phe Lys
        35                  40                  45

Gln Arg Phe Ser Glu Glu Asn Ser Lys Thr Asp Gln Asn Leu Gly Lys
    50                  55                  60

Ala Glu Glu
65

<210> SEQ ID NO 108
<211> LENGTH: 62
<212> TYPE: PRT
<213> ORGANISM: Unknown
<220> FEATURE:
<223> OTHER INFORMATION: Description of Unknown:
      sequence

<400> SEQUENCE: 108

Arg Glu Ile Val Lys Leu Cys Ser Gln Tyr Gln Asn Gln Ala Lys Asn
1               5                  10                  15

Gly Ile Leu Phe Cys Thr Arg Glu Asn Asp Pro Ile Arg Gly Pro Asp
            20                  25                  30

Gly Lys Met His Gly Asn Leu Cys Ser Met Cys Gln Ala Tyr Phe Gln
        35                  40                  45

Ala Glu Asn Glu Glu Lys Lys Lys Ala Glu Ala Arg Ala Arg
    50                  55                  60

<210> SEQ ID NO 109
<211> LENGTH: 68
<212> TYPE: PRT
<213> ORGANISM: Unknown
<220> FEATURE:
<223> OTHER INFORMATION: Description of Unknown:
      sequence

<400> SEQUENCE: 109

Glu Ser Gly Lys Ala Thr Ser Tyr Ala Glu Leu Cys Ser Glu Tyr Arg
```

```
                1               5                  10                 15
Lys Leu Val Arg Asn Gly Lys Leu Ala Cys Thr Arg Glu Asn Asp Pro
                20                 25                 30

Ile Gln Gly Pro Asp Gly Lys Val His Gly Asn Thr Cys Ser Met Cys
                35                 40                 45

Glu Val Phe Phe Gln Ala Glu Glu Glu Lys Lys Lys Lys Glu Gly
                50                 55                 60

Lys Ser Arg Asn
65

<210> SEQ ID NO 110
<211> LENGTH: 59
<212> TYPE: PRT
<213> ORGANISM: Unknown
<220> FEATURE:
<223> OTHER INFORMATION: Description of Unknown:
      sequence

<400> SEQUENCE: 110

Ala Ser Phe Glu Glu Leu Cys Ser Glu Tyr Arg Lys Ser Arg Lys Asn
1               5                  10                 15

Gly Arg Leu Phe Cys Thr Arg Glu Asn Asp Pro Ile Gln Gly Pro Asp
                20                 25                 30

Gly Lys Met His Gly Asn Thr Cys Ser Met Cys Glu Ala Phe Phe Gln
                35                 40                 45

Gln Glu Glu Arg Ala Arg Ala Lys Ala Lys Arg
                50                 55

<210> SEQ ID NO 111
<211> LENGTH: 62
<212> TYPE: PRT
<213> ORGANISM: Unknown
<220> FEATURE:
<223> OTHER INFORMATION: Description of Unknown:
      sequence

<400> SEQUENCE: 111

Glu Ala Ala Lys Glu Ile Cys Ser Glu Phe Arg Asp Gln Val Arg Asn
1               5                  10                 15

Gly Thr Leu Ile Cys Thr Arg Glu His Asn Pro Val Arg Gly Pro Asp
                20                 25                 30

Gly Lys Met His Gly Asn Lys Cys Ala Met Cys Ala Ser Val Phe Lys
                35                 40                 45

Leu Glu Glu Glu Glu Lys Lys Asn Asp Lys Glu Lys Gly
                50                 55                 60

<210> SEQ ID NO 112
<211> LENGTH: 62
<212> TYPE: PRT
<213> ORGANISM: Unknown
<220> FEATURE:
<223> OTHER INFORMATION: Description of Unknown:
      sequence

<400> SEQUENCE: 112

Glu Ala Val Gln Glu Leu Cys Ser Glu Tyr Arg His Tyr Val Arg Asn
1               5                  10                 15

Gly Arg Leu Pro Cys Thr Arg Glu Asn Asp Pro Ile Glu Gly Leu Asp
                20                 25                 30

Gly Lys Ile His Gly Asn Thr Cys Ser Met Cys Glu Ala Phe Phe Gln
                35                 40                 45
```

Gln Glu Ala Lys Glu Lys Glu Arg Ala Glu Pro Arg Ala Lys
    50                  55                  60

<210> SEQ ID NO 113
<211> LENGTH: 63
<212> TYPE: PRT
<213> ORGANISM: Unknown
<220> FEATURE:
<223> OTHER INFORMATION: Description of Unknown:
      sequence

<400> SEQUENCE: 113

Glu Ala Glu Lys Glu Thr Cys Asp Glu Phe Arg Arg Leu Leu Gln Asn
1               5                   10                  15

Gly Lys Leu Phe Cys Thr Arg Glu Asn Asp Pro Val Arg Gly Pro Asp
            20                  25                  30

Gly Lys Thr His Gly Asn Lys Cys Ala Met Cys Lys Ala Val Phe Gln
        35                  40                  45

Lys Glu Asn Glu Glu Arg Lys Arg Lys Glu Glu Asp Gln Arg
    50                  55                  60

<210> SEQ ID NO 114
<211> LENGTH: 57
<212> TYPE: PRT
<213> ORGANISM: Unknown
<220> FEATURE:
<223> OTHER INFORMATION: Description of Unknown:
      sequence

<400> SEQUENCE: 114

Gly Asn Thr Gln Asp Glu Cys Ala Glu Tyr Arg Glu Gln Met Lys Asn
1               5                   10                  15

Gly Arg Leu Ser Cys Thr Arg Glu Ser Asp Pro Val Arg Asp Ala Asp
            20                  25                  30

Gly Lys Ser Tyr Asn Asn Gln Cys Thr Met Cys Lys Ala Lys Leu Glu
        35                  40                  45

Arg Glu Ala Glu Arg Lys Asn Glu Tyr
    50                  55

<210> SEQ ID NO 115
<211> LENGTH: 63
<212> TYPE: PRT
<213> ORGANISM: Unknown
<220> FEATURE:
<223> OTHER INFORMATION: Description of Unknown:
      sequence

<400> SEQUENCE: 115

Glu Ser Gly Lys Asp Thr Cys Asp Glu Phe Arg Ser Gln Met Lys Asn
1               5                   10                  15

Gly Lys Leu Ile Cys Thr Arg Glu Ser Asp Pro Val Arg Gly Pro Asp
            20                  25                  30

Gly Lys Thr His Gly Asn Lys Cys Thr Met Cys Lys Glu Lys Leu Glu
        35                  40                  45

Arg Glu Ala Ala Glu Lys Lys Lys Glu Asp Glu Asp Arg Ser
    50                  55                  60

<210> SEQ ID NO 116
<211> LENGTH: 63
<212> TYPE: PRT
<213> ORGANISM: Unknown
<220> FEATURE:

<223> OTHER INFORMATION: Description of Unknown:
      sequence

<400> SEQUENCE: 116

Asn Asp Lys Glu Asp Leu Cys Arg Glu Phe Arg Ser Met Gln Arg Asn
1               5                   10                  15

Gly Lys Leu Ile Cys Thr Arg Glu Asn Asn Pro Val Arg Gly Pro Tyr
            20                  25                  30

Gly Lys Met His Ile Asn Lys Cys Ala Met Cys Gln Ser Ile Phe Asp
        35                  40                  45

Arg Glu Ala Asn Glu Arg Lys Lys Lys Asp Glu Glu Lys Ser Ser
    50                  55                  60

<210> SEQ ID NO 117
<211> LENGTH: 62
<212> TYPE: PRT
<213> ORGANISM: Unknown
<220> FEATURE:
<223> OTHER INFORMATION: Description of Unknown:
      sequence

<400> SEQUENCE: 117

Asn Asn Ala Lys Asp Glu Cys Ser Glu Phe Arg Asn Tyr Ile Arg Asn
1               5                   10                  15

Asn Glu Leu Ile Cys Pro Arg Glu Asn Asp Pro Val His Gly Ala Asp
            20                  25                  30

Gly Lys Phe Tyr Thr Asn Lys Cys Tyr Met Cys Arg Ala Val Phe Leu
        35                  40                  45

Thr Glu Ala Leu Glu Arg Ala Lys Leu Gln Glu Lys Pro Ser
    50                  55                  60

<210> SEQ ID NO 118
<211> LENGTH: 62
<212> TYPE: PRT
<213> ORGANISM: Unknown
<220> FEATURE:
<223> OTHER INFORMATION: Description of Unknown:
      sequence

<400> SEQUENCE: 118

Ser Leu Asp Ser Glu Met Cys Lys Asp Tyr Arg Val Leu Pro Arg Ile
1               5                   10                  15

Gly Tyr Leu Cys Pro Lys Asp Leu Lys Pro Val Cys Gly Asp Asp Gly
            20                  25                  30

Gln Thr Tyr Asn Asn Pro Cys Met Leu Cys His Glu Asn Leu Ile Arg
        35                  40                  45

Gln Thr Asn Thr His Ile Arg Ser Thr Gly Lys Cys Glu Glu
    50                  55                  60

<210> SEQ ID NO 119
<211> LENGTH: 3192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
atgaagatag ccacagtgtc agtgcttctg cccttggctc tttgcctcat acaagatgct      60
gccagtaaga atgaagatca ggaaatgtgc catgaatttc aggcatttat gaaaaatgga     120
aaactgttct gtccccagga taagaaattt tttcaaagtc ttgatggaat aatgttcatc     180

```
aataaatgtg ccacgtgcaa aatgatactg gaaaaagaag caaaatcaca gaagagggcc    240
aggcatttag caagagctcc caaggctact gccccaacag agctgaattg tgatgatttt    300
aaaaaaggag aaagagatgg ggattttatc tgtcctgatt attatgaagc tgtttgtggc    360
acagatggga aaacatatga caacagatgt gcactgtgtg ctgagaatgc gaaaaccggg    420
tcccaaattg gtgtaaaaag tgaagggaa tgtaagagca gtaatccaga gcaggatgta    480
tgcagtgctt ttcggcccctt tgttagagat ggaagacttg gatgcacaag ggaaaatgat    540
cctgttcttg gtcctgatgg gaagacgcat ggcaataagt gtgcaatgtg tgctgagctg    600
tttttaaaag aagctgaaaa tgccaagcga gagggtgaaa ctagaattcg acgaaatgct    660
gaaaaggatt tttgcaagga atatgaaaaa caagtgagaa atggaaggct tttttgtaca    720
cgggagagtg atccagtccg tggccctgac ggcaggatgc atggcaacaa atgtgccctg    780
tgtgctgaaa ttttcaagca gcgttttttca gaggaaaaca gtaaaacaga tcaaaatttg    840
ggaaaagctg aagaaaaaac taaagttaaa agagaaattg tgaaactctg cagtcaatat    900
caaaatcagg caaagaatgg aatacttttc tgtaccagag aaaatgaccc tattcgtggt    960
ccagatggga aaatgcatgg caacttgtgt tccatgtgtc aagcctactt ccaagcagaa   1020
aatgaagaaa agaaaaaggc tgaagcacga gctagaaaca aaagagaatc tggaaaagca   1080
acctcatatg cagagctttg cagtgaatat cgaaagcttg tgaggaacgg aaaacttgct   1140
tgcaccagag agaacgatcc tatccagggc ccagatggga agtgcatgg caacacctgc   1200 tccatgtgtg aggtcttctt ccaagcagaa gaagaagaaa agaaaaagaa ggaaggtaaa   1260
tcaagaaaca aaagacaatc taagagtaca gcttcctttg aggagttgtg tagtgaatac   1320
cgcaaatcca ggaaaaacgg acggcttttt tgcaccagag agaatgaccc catccagggc   1380
ccagatggaa aaatgcatgg caacacctgc tccatgtgtg aggccttctt tcaacaagaa   1440
gaaagagcaa gagcaaaggc taaaagagaa gctgcaaagg aaatctgcag tgaatttcgg   1500
gaccaagtga ggaatggaac acttatatgc accagggagc ataatcctgt ccgtggccca   1560
gatggcaaaa tgcatggaaa caagtgtgcc atgtgtgcca gtgtgttcaa acttgaagaa   1620
gaagagaaga aaaatgataa agaagaaaaa gggaaagtcg aggctgaaaa agttaagaga   1680
gaagcagttc aggagctgtg cagtgaatat cgtcattatg tgaggaatgg acgactcccc   1740
tgtaccagag agaatgatcc tattgagggt ctagatggga aaatccacgg caacacctgc   1800
tccatgtgtg aagccttctt ccagcaagaa gcaaagaaa aagaagagc tgaacccaga   1860 gcaaagtca aagagaagc tgaaaaggag acatgcgatg aatttcggag acttttgcaa   1920
aatggaaaac ttttctgcac aagagaaaat gatcctgtgc gtggcccaga tggcaagacc   1980
catggcaaca agtgtgccat gtgtaaggca gtcttccaga agaaaatga ggaaagaaag   2040 aggaaagaag aggaagatca gagaaatgct gcaggacatg gttccagtgg tggtggagga   2100
ggaaacactc aggacgaatg tgctgagtat cgggaacaaa tgaaaatgg aagactcagc   2160 tgtactcggg agagtgatcc tgtacgtgat gctgatggca aatcgtacaa caatcagtgt   2220
accatgtgta aagcaaaatt ggaaagagaa gcagagagaa aaatgagta ttctcgctcc   2280 agatcaaatg ggactggatc agaatcaggg aaggatacat gtgatgagtt tagaagccaa   2340
atgaaaaatg gaaaactcat ctgcactcga gaaagtgacc ctgtccgggg tccagatggc   2400
aagacacatg gcaataagtg tactatgtgt aaggaaaaac tggaaaggga agcagctgaa   2460
aaaaaaagga aagaggatga agacaggagc aatacaggag aaaggagcaa tacaggagaa   2520
```

```
aggagcaatg acaaagagga tctgtgtcgt gaatttcgaa gcatgcagag aaatggaaag    2580
cttatctgca ccagagaaaa taaccctgtt cgaggcccat atggcaagat gcacatcaat    2640
aaatgtgcta tgtgtcagag catctttgat cgagaagcta atgaaagaaa aagaaagat    2700 gaagagaaat caagtagcaa gccctcaaat aatgcaaagg atgagtgcag tgaatttcga    2760
aactatataa ggaacaatga actcatctgc cctagagaga atgacccagt gcacggtgct    2820
gatggaaagt tctatacaaa caagtgctac atgtgcagag ctgtctttct aacagaagct    2880
ttggaaaggg caaagcttca agaaaagcca tcccatgtta gagcttctca agaggaagac    2940
agcccagact ctttcagttc tctggattct gagatgtgca aagactaccg agtattgccc    3000
aggataggtt atctttgtcc aaaggattta aagcctgtct gtggtgacga tggccaaacc    3060
tacaacaatc cttgcatgct ctgtcatgaa aacctgatac gccaaacaaa tacacacatc    3120
cgcagtacag ggaagtgtga ggagagcagc accccaggaa ccaccgcagc cagcatgccc    3180
ccgtctgacg aa                                                       3192
```

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 120

His His His His His His
1               5

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Ala Pro Phe
1

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
atgcgtcgta tgcgtcgtat g                                             21

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtggtggtgg tggtggtg                                                 18

```
<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ttgatatgcc tcctaaattt tt                                                    22

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
taggcgcgcc tattctaatg c                                                     21
```

COMPOSITIONS AND METHODS FOR TREATMENT OF NETHERTON SYNDROME WITH LEKTI EXPRESSING RECOMBINANT MICROBES

RELATED APPLICATIONS

This application claims priority to U.S. Provisional Application 62/521,050, filed on Jun. 16, 2017, the entire contents of which are incorporated by reference in its entirety herein.

The instant application contains a Sequence Listing which has been submitted electronically in ASCII format and is hereby incorporated by reference in its entirety. Said ASCII copy, created on Jul. 20, 2018, is named 129062-00420_SL.txt and is 54,743 bytes in size.

FIELD OF THE DISCLOSURE

The present disclosure relates to methods, kits, and compositions for treating or ameliorating the effects of Netherton Syndrome using one or more recombinant microorganisms that are genetically modified to express one or more therapeutic LEKTI domains on the skin of a subject.

BACKGROUND OF THE INVENTION

The epidermis, the squamous stratified epithelium of the skin, consists of multiple sublayers and is one of the most important barriers of the body against the outside world. The stratum corneum is the outermost layer of the epidermis and develops as a result of the final anucleated step in keratinocyte differentiation from the cells in nucleated epidermal layers. Although the stratum corneum is recognized as the most important physical barrier, the nucleated epidermal layers are also significant in barrier function (Proksch, Brandner et al. 2008). Together, the skin barrier protects against extensive water loss in one direction (inside-outside barrier) and against the invasion of harmful substances from the environment (outside-inside barrier) (Proksch, Brandner et al, 2008). The maintenance of the barrier is also important for balanced proliferation in the basal layer and preservation of the calcium ion gradient and thus proper epidermal differentiation (Lee, Jeong et al. 2006).

A number of current limitations exist in the treatment of skin. Many treatments, such as topical corticosteroids or biologics, do not treat the underlying issues of deficient intrinsic protein in the epidermis or imbalances in the microbial diversity in the skin. While recombinant proteins represent a promising group of therapeutic agents in the treatment of skin disease, several problems accompany their use in the context of the skin.

Traditional methods purify and concentrate recombinant proteins that are extracted from bacterial systems, and then incorporate such preparations into a delivery system. The purification of recombinant proteins is often a very costly method of obtaining protein. Moreover, a number of problems are associated with these traditional methods, including proteolytic degradation, inefficient delivery, and the need for repeated application overtime to achieve therapeutic effect.

One skin disease that would benefit from improved treatment modalities is Netherton Syndrome (NS). NS is a rare autosomal skin disease manifested as severe skin inflammation and scaling, hair shaft defects, constant allergic symptoms, and immune system problems. Newborns with NS often have red and scaly skin that may leak fluid, which creates a risk of dehydration and infections of the skin or throughout the body. Affected children may also fail to grow at a normal rate. The health of older children and adults with NS typically improves, but those individuals are often underweight and of short stature. Most people with NS also have immune system problems such as food allergies, hay fever, asthma, or eczema.

NS is caused by a loss-of-function defect in the gene SPINK5 (serine protease inhibitor of kazal type 5), which encodes lymphoepithelial kazal type related inhibitor type 5 (LEKTI) protein. LEKTI is a multi-domain serine protease inhibitor that is normally expressed in all stratified epithelial cells and the Hassal corpuscules of the thymus. The SPINK5 gene encoding LEKTI is located on chromosome 5 among a cluster of other SPINK genes (e.g. SPINK6 and SPINK9), and comprises 33 exons encoding 15 inhibitory domains separated by linker regions. SPINK5 stands out among the other SPINK genes for the large number of inhibitory domains it encodes. Additionally, the SPINK5 gene is transcribed into three different transcripts, resulting in three different LEKTI proteins that differ in the C-terminal region; i.e. a 145 kDa full length protein having inhibitory domains D1-D15, a 125 kDa (short) protein having inhibitory domains D1-D12, and a 148 kDa (long) protein having an extended linker region 13.

The LEKTI protein is a Kazal-type-related inhibitor. The Kazal motif is defined by the presence of six cysteine residues positioned at specific distances to allow formation of three disulfide bonds in a 1-5, 2-4, and 3-6 pattern. Two of the domains of LEKTI (D2 and D5) form this six cysteine motif, while other domains share four cysteine residues, which produce a rigid inhibitory loop believed to mimic the substrate of target proteases and inactivate the target protease catalytic site.

The LEKTI protein requires proteolytic cleavage for activation of its inhibitory function against many proteases. Specifically, the full length protein is cleaved into domains D1-D5 and D6-D15. The D6-D15 domains are then further cleaved in multiple steps into D6-D9 and D10-D15, →D6 and D7-D9→D7 and D8-D9→D8. This process results in LEKTI proteins comprising between one and six inhibitory domains, with each protein having different inhibitory functions. For example, the various LEKTI inhibitory fragments can inhibit various kallikrein-related peptidases (KLK) such as KLK5, KLK7, and KLK14.

Defective LEKTI proteins can result from substitution, insertion, or deletion mutation of the SPINK5 gene, often causing nonsense or frameshifts mutations that result in premature termination codons. Other mutations in splice-sites bases can lead to abnormal splicing events of the transcribed SPINK5 gene. Thus, many SPINK5 mutations result in the complete absence of LEKTI domain synthesis. LEKTI deficiency or defective LEKTI may result in deregulated protease activity causing skin desquamation and epidermal permeability through impaired epidermal differentiation and lipid metabolism, which leads to a defective skin barrier. Furthermore, unregulated activity of some KLK proteins leads to desmosome cleavage and stratum corneum detachment.

Netherton Syndrome is an orphan disease with no specific treatment available. In view of the foregoing, there is a need for novel therapeutic agents for treatment of NS. The present application is directed to meeting these and other needs.

SUMMARY OF THE INVENTION

According to one aspect, the present disclosure provides a composition for the treatment of a skin disease comprising a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

According to some embodiments, the microbe is adapted to live for a controlled duration on the surface of the mammal's skin to provide a continuous supply of LEKTI protein domains. According to some embodiments, the LEKTI protein domains are effective to ameliorate the symptoms of Netherton Syndrome. In one embodiment, the LEKTI domain is Domain 6.

According to some embodiments, the microbe is genetically modified by transfection/transformation with a recombinant DNA plasmid encoding the LEKTI protein domains. In some embodiments, the LEKTI domains are operably linked to one or more recombinant protein domains that are effective to enhance secretion from the microbe and/or penetration of the mammal's skin. According to some embodiments, at least one LEKTI domain is operably linked to a SecA domain. According to some embodiments, at least one LEKTI domain is operably linked to an RMR domain.

According to some embodiments, the microbe is adapted to multiply on the skin of the mammal.

According to some embodiments, expression of at least one LEKTI domain is controlled by an operon and the amount of LEKTI provided to the mammal's skin is proportional to the availability of an extrinsic factor. In some embodiments, the expression of at least one LEKTI domain is controlled by a promoter that is constitutively active.

According to some embodiments, the microbe has been genetically modified by transfection/transformation with a recombinant DNA plasmid encoding the LEKTI protein domains and one or more antibiotic resistance genes.

According to some embodiments, the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or Oenococcus, and mixtures thereof.

According to one aspect, the present disclosure provides a method of treating or ameliorating the effects of a skin disease of a mammal in need thereof comprising providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin.

According to some embodiments, the microbe is adapted to live for a controlled duration on the surface of the mammal's skin to provide a continuous supply of LEKTI protein domains.

According to another aspect, the present disclosure provides a kit for the treatment or amelioration of the effects of a skin disease of a mammal in need thereof comprising (1) a composition comprising a microbe that is genetically modified to express one or more LEKTI protein domains, wherein the LEKTI protein domains are effective to penetrate one or more layers of the mammal's skin and effective to inhibit serine protease activity of at least one serine protease in or on the mammal's skin, and (2) reagents for applying the composition to the skin of the mammal.

According to some embodiments, the microbes are adapted to live for a controlled duration on the surface of the mammal's skin to provide a continuous supply of LEKTI protein domains.

According to one aspect, the present disclosure provides a composition for the treatment of skin disease comprising a microbe comprising pJB38-LEKTI-complete plasmid construct.

According to some embodiments, the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof.

According to one aspect, the present disclosure provides a composition comprising pJB38-LEKTI-complete plasmid construct. In some embodiments, the pJB38-LEKTI-complete plasmid construct is expressed in a microbe selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof.

BRIEF DESCRIPTION OF THE DRAWINGS

FIG. 7A and FIG. 7B show recombinantly produced LEKTI Domain 6 inhibits trypsin in vitro. FIG. 7A is a schematic of the experiment that was performed. FIG. 7B is a graph that shows trypsin activity.

FIG. 8A and FIG. 8B show recombinantly produced LEKTI Domain 6 (ct His6 tag) inhibits trypsin in vitro compared to LEKTI domains 10-15. FIG. 8A is a schematic of the experiment that was performed. FIG. 8B is a graph that shows trypsin activity.

FIG. 9A and FIG. 9B show recombinantly produced LEKTI Domain 6 inhibits KLK7 in vitro similar to inhibition of KLK7 by LEKTI domains 10-15. FIG. 9A is a schematic of the experiment that was performed. FIG. 9B is a graph that shows KLK7 activity.

FIG. 10A and FIG. 10B show recombinantly produced LEKTI Domain 6 inhibits KLK5 in vitro at nanomolar concentrations. FIG. 10A is a schematic of the experiment that was performed. FIG. 10B is a graph that shows KLK5 activity.

DETAILED DESCRIPTION OF THE INVENTION

Figure 1:
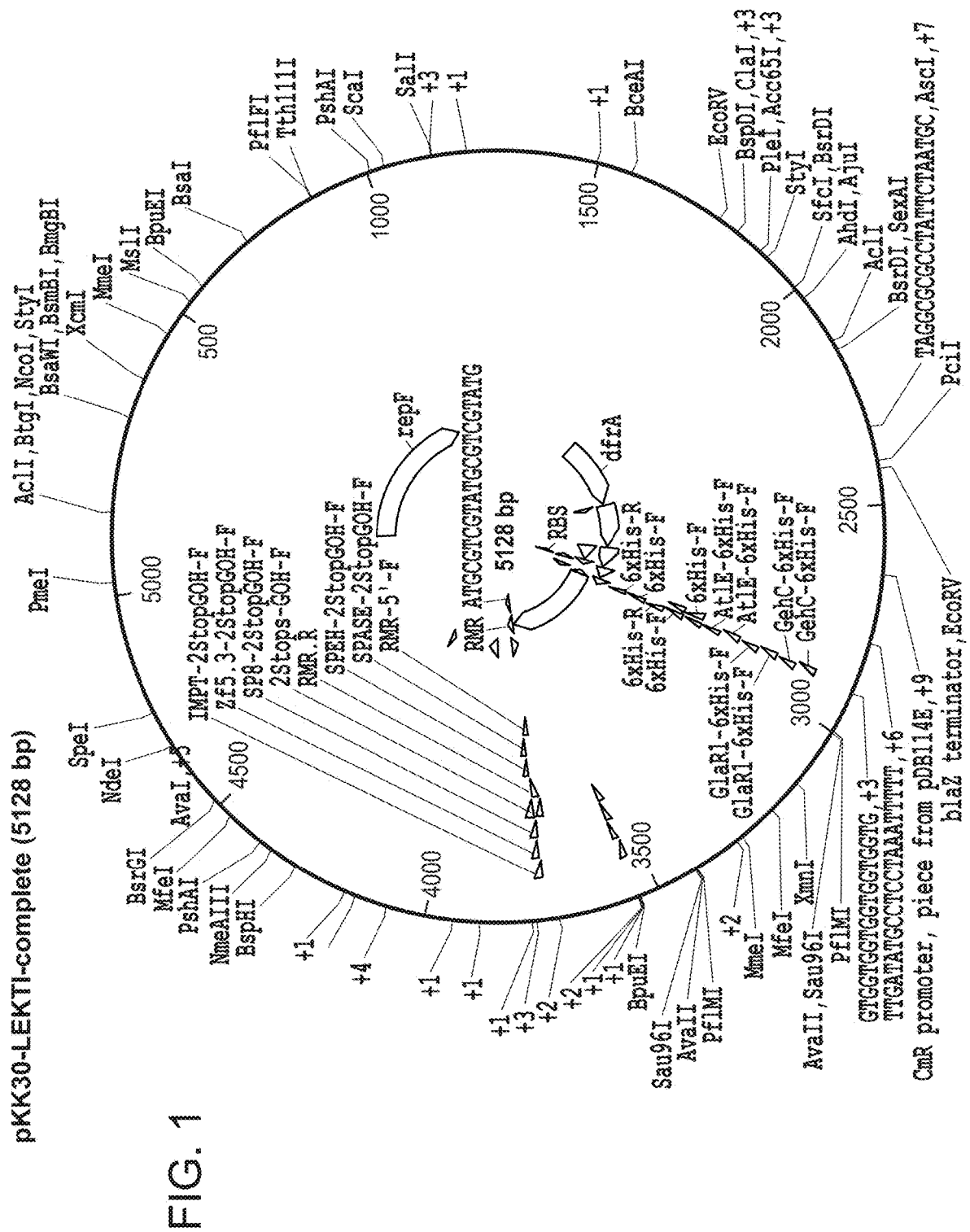
FIG. 1 shows a vector construct comprising the therapeutic LEKTI domains of the present invention. The protein coding regions of the plasmid comprise SecA, 6×His tag, LEKTI D8-11, and RMR tag, operably linked to each other and under the control of a CmR promoter.
Figure 2:
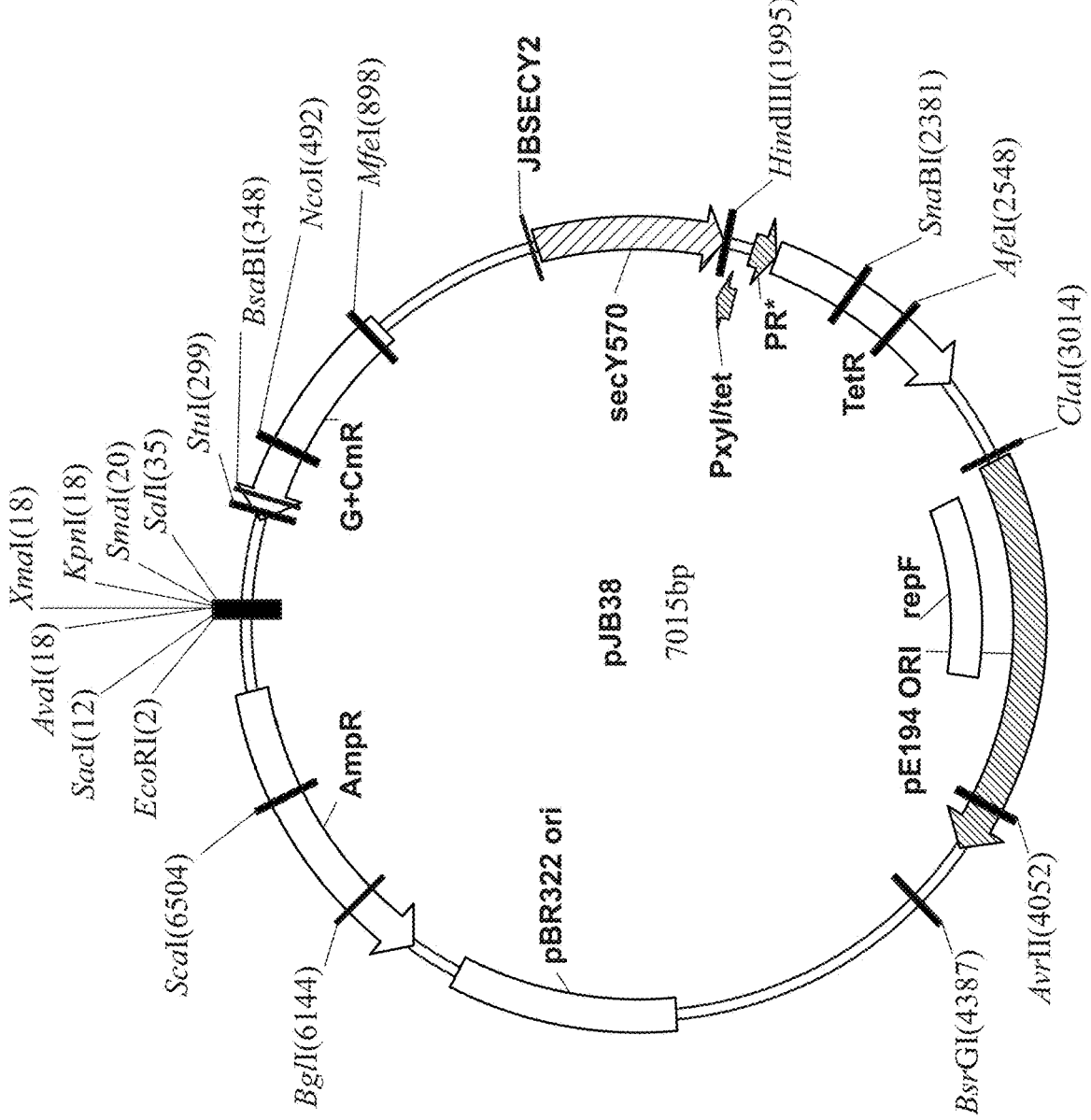
FIG. 2 shows a vector construct of the pJB38 plasmid according to some embodiments of the present invention.

One aspect of the present disclosure provides skin-colonizing bacteria that are genetically altered to express recombinant proteins to treat or ameliorate Netherton Syndrome. The genetically altered protein-producing bacteria are able to treat NS by expressing and, optionally, secreting a therapeutic protein that treats the underlying cause of the disease or its symptoms. According to some embodiments, the therapeutic protein comprises one or more LEKTI domains that are effective to inhibit serine proteases within or on the skin of a mammal. According to some embodiments, the recombinant LEKTI domains compensate for the defective endogenous LEKTI protein naturally produced by the skin in the mammal. According to some embodiments, the genetically altered bacteria are able to self-replicate while retaining the ability to produce the recombinant protein, thereby providing a continuous supply of therapeutic agent.

According to some embodiments, the disclosure provides a composition for the treatment of a skin disease comprising a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

As used herein the term "skin disease" and grammatical variations thereof means a skin state or condition that is generally undesirable or deleterious compared to the normal or baseline condition of human skin. Examples of abnormal skin conditions include, without limitation, Netherton Syndrome, psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the term "genetically modified" and grammatical variations thereof are used to describe a microbial organism (e.g. bacteria) that has been genetically modified or engineered by the introduction of DNA prepared outside the microbe. For example, the introduction of plasmid DNA containing new genes into bacteria will allow the bacteria to express those genes. Alternatively, the DNA containing new genes can be introduced to the bacteria and then integrated into the bacteria's genome, where the bacteria will express those genes.

As used herein, the terms "treat," "treating," "treatment" and grammatical variations thereof mean providing to a subject a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

In the present invention, the subject may be a mammal. As used herein, a "mammal" and grammatical variations thereof means any category of mammal. In the present invention, mammals include, for example, humans, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. Preferably, the mammal is a human.

As used herein, the term "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a composition according to the invention will be that amount of the composition, which is the lowest dose effective to produce the desired effect. The effective dose of a composition of the present invention may be administered as two, three, four, five, six or more sub-doses, administered separately at appropriate intervals throughout the day.

Microbial compositions: According to some embodiments, the disclosure provides microbial compositions comprising one or more of a wide range of bacteria suitable for use on a mammal's skin. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Pediococcus, Leuconostoc,* or *Oenococcus.* According to some embodiments, microbial compositions comprise one or more of *Staphylococcus* warneri, *Streptococcus pyogenes, Streptococcus mitis, Propionibacterium acnes, Corynebacterium* spp., *Acinetobacter johnsonii, Pseudomonas aeruginosa.* According to some embodiments, other related or similar species found on the skin are used.

Certain embodiments involve the use of bacterium *Staphylococcus epidermidis*. According to some embodiments, the strain of *S. epidermidis* to be used is incapable of producing biofilms. An example of this is *S. epidermidis* strain ATCC 12228 or NRRL B-4268.

According to some embodiments, the recombinant microbe is adapted to live indefinitely or for a controlled duration on the surface of the mammal's skin to provide a continuous supply of LEKTI protein domains. In some embodiments, the recombinant microbe lives alongside commensal microorganisms naturally occurring on the mammal's skin. In some embodiments, the recombinant microbe lives to the exclusion of commensal microorganisms that naturally occur on the mammal's skin. According to some embodiments, the recombinant microbe is adapted to multiply on the skin of the mammal. In other embodiments, the recombinant microbe is no longer alive, but contains effective amounts of a therapeutic polypeptide, e.g. LEKTI or therapeutically effective domain(s) thereof. Such cells may be intact or not depending upon the particulars of delivering the therapeutic peptide (or domain(s) thereof) to the target site.

As used herein, the term "recombinant" and grammatical variations thereof means relating to or denoting an organism, protein, or genetic material formed by or using recombined DNA comprising DNA pieces from different sources or from different parts of the same source. For example, the term "recombinant DNA" means a DNA molecule formed through recombination methods to splice fragments of DNA from a different source or from different parts of the same source. In some embodiments, two or more different sources of DNA are cleaved using restriction enzymes and joined together using ligases. As another example, the term "recombinant protein" or "recombinant domains" and grammatical variations thereof means a protein molecule formed through recombination methods originating from spliced fragments of DNA from a different source or from different parts of the same source. As another example, the term "recombinant microbe" or "recombinant bacteria" and grammatical variations thereof mean a microbe/bacteria that comprises one or more recombinant DNA/protein molecules.

According to some embodiments, the microbe is selected from the group consisting of *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Enterococcus, Pediococcus, Leuconostoc,* or *Oenococcus*, and mixtures thereof.

LEKTI gene: According to some embodiments, the recombinant microbe is engineered to express a mammalian gene encoding LEKTI protein. The LEKTI gene can be obtained from any mammal, such as mouse, rat, rabbit, goat, sheep, horse, cow, dog, primate, or human gene sequences. According to some embodiments, the LEKTI gene sequence is a human gene sequence. According to some embodiments, the recombinant microbe is engineered to comprise a fragment of the LEKTI gene.

According to some embodiments, the recombinant protein expressed by the engineered microbe comprises LEKTI D8-11. In one embodiment, the fragment comprises one or more LEKTI domains. In a specific embodiment, the LEKTI domain is Domain 6.

According to some embodiments, the recombinant microbe comprises a sequence as disclosed herein that has at least about 75% identity, or 80% identity, or 85% identity, or 90% identity, or 95% identity to any one or more of the SEQ ID NOS listed herein. As used herein, the term "identity" and grammatical versions thereof means the extent to which two nucleotide or amino acid sequences have the same residues at the same positions in an alignment. Percent (%) identity is calculated by multiplying the number of matches in a sequence alignment by 100 and dividing by the length of the aligned region, including internal gaps.

According to some embodiments, the recombinant protein expressed by the engineered microbe comprises one or more protease inhibitory domains of the LEKTI protein. Some non-limiting examples include one or more of domains D1, D2, D3, D4, D5, D6, D7, D8, D9, D10, D11, D12, D13, D14, and D15. According to some embodiments, the recombinant protein expressed by the engineered microbe comprises LEKTI inhibitory domain 6 or domains D8 to D11.

According to some embodiments, the LEKTI protein domains are effective to ameliorate the symptoms of Netherton Syndrome. As used herein, the terms "ameliorate", "ameliorating" and grammatical variations thereof mean to decrease the severity of the symptoms of a disease in a subject. In some embodiments, the LEKTI protein domains act as a competitive or non-competitive inhibitor of one or more proteases present on or in the skin of a mammal. In some embodiments, the LEKTI protein domain acts as a serine protease inhibitor. As used herein, the terms "protease" and "proteinase" are used interchangeably, with both terms referring to an enzyme that performs proteolysis.

According to some embodiments, the microbe is genetically modified by transfection/transformation with a recombinant DNA plasmid encoding the LEKTI protein domains. Other conventional or to-be-discovered methods for introducing DNA into a microbe may also be used in the present invention. According to some embodiments, the recombinant DNA plasmid comprises sequences encoding the LEKTI protein domain and one or more secretory peptides and/or cell penetration peptides. According to some embodiments, the LEKTI domains are operably linked to one or more recombinant protein domains that are effective to enhance secretion from the microbe and/or penetration of the mammal's skin.

The term "operably linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

As used herein the term "secretory peptides" or "secretory sequences" or "secretion tags" or "signal peptides" or "export signals" and grammatical variations thereof means any peptide sequence that is capable of targeting the synthesized protein to the secretory pathway of a cell. In some embodiments, the secretory peptide may be positioned on the N-terminal end of a recombinant protein, and may co-translationally or post-translationally target the tagged protein for secretion. According to some embodiments, at least one LEKTI domain is operably linked to a SecA domain.

Secretion peptides: According to some embodiments, the therapeutic LEKTI domain is operably linked to one or more secretion signals or export signals that tag the protein for transport through the secretory pathway. Any secretion signal that facilitates exit of the LEKTI protein out of the bacterial cell may be used as a secretion peptide. Non-limiting examples of secretion peptides signals are set forth in Table 1, below:

TABLE 1

| Amino Acid Sequence | SEQ ID NO: |
|---|---|
| MKKLAFAITAASGAAAVLSHHDAEA | SEQ ID NO: 9 |
| WLDNRAFSKKFVPVVMATSVALFFLNLAFA | SEQ ID NO: 10 |
| MAKKFNYKLPSMVALTLFGTAFTAHQANA | SEQ ID NO: 11 |
| MKKRFLSICTMTIAALATTTMVNTSYA | SEQ ID NO: 12 |
| NLKKQSKLILIFICIFTFFIMIIQSQFLMG | SEQ ID NO: 13 |
| MKIFKLTSLTLAALTLAFPFSHVAQA | SEQ ID NO: 14 |
| MKKTVIASTLAVSLGIAGYGLSGHEAH | SEQ ID NO: 15 |
| MKKNKFLVYLLSTALITPTFATQTAFA | SEQ ID NO: 16 |
| MKTRQNKYSIRKFSVGASSILIAALLFMGGGSAQA | SEQ ID NO: 17 |
| MKNNNETRRFSIRKYTVGVVSIITGITIFVSGQHAQA | SEQ ID NO: 18 |
| MKKKLSYMITIMLAFTLSLALGLFFNSAHA | SEQ ID NO: 19 |

According to some embodiments, the therapeutic LEKTI domain is operably linked to one or more signal sequences derived from endogenous proteins of *Staphylococcus epidermidis*. Non-limiting examples of secretion signal peptides derived from endogenous proteins of *Staphylococcus epidermidis* are set forth in Table 2 below:

TABLE 2

*Staphylococcus epidermidis*

| Protein Name | Amino Acid Length | Signal Sequence | SEQ ID NO |
|---|---|---|---|
| Serine-aspartate repeat-containing protein F | 45 | MKKRRQGPINKRVDFLSNKVNK YSIRKFTVGTASILVGATLMFGA | SEQ ID NO: 20 |
| Glutamyl endopeptidase | 27 | MKKRFLSICTMTIAALATTTMVN TSYA | SEQ ID NO: 21 |
| Bifunctional autolysin | 29 | MAKKFNYKLPSMVALTLFGTAF TAHQANA | SEQ ID NO: 22 |
| Serine-aspartate repeat-containing protein G | 50 | MIKKNNLLTKKKPIANKSNKYAI RKFTVGTASIVIGAALLFGLGHN EAKA | SEQ ID NO: 23 |
| Biofilm PIA synthesis deacetylase icaB | 30 | MKPFKLIFISALMILIMTNATPISH LNAQA | SEQ ID NO: 24 |
| Lipase | 35 | MKTRQNKYSIRKFSVGASSILIAA LLFMGGGSAQA | SEQ ID NO: 25 |
| Epidermin leader peptide-processing serine protease epiP | 23 | MNKFKFFIVFLILSLVFLQNEYA | SEQ ID NO: 26 |
| Fibrinogen-binding protein | 51 | MINKKNNLLTKKKPIANKSNKY AIRKFTVGTASIVIGATLLFGLGH NEAK A | SEQ ID NO: 27 |
| Staphylococcal secretory antigen ssaA | 26 | MKKIATATIATAGIATFAFAHHD AQA | SEQ ID NO: 28 |
| Extracellular elastase | 28 | MKNFSKFALTSIAALTVASPLVN TEVDA | SEQ ID NO: 29 |
| n/a | 37 | MKNNNETRRFSIRKYTVGVVSIIT GITIFVSGQHAQA | SEQ ID NO: 30 |
| Uncharacterized lipoprotein SE_0145 | 19 | MRYLKRITIYISLLILVSG | SEQ ID NO: 31 |
| Foldase protein prsA | 20 | MKLMNKIIVPVTASALLLGA | SEQ ID NO: 32 |
| Probable cell wall amidase lytH | 40 | MKKIDSWLTKHGLKNRLTLVVI VIFIIFLILLFMFVNLSD | SEQ ID NO: 33 |
| Membrane protein oxaA 2 | 19 | MKKKALLPLFLGIMIFLAG | SEQ ID NO: 34 |
| Probable transglycosylase isaA | 28 | MKKTVIASTLAVSLGIAGYGLSG HEAHA | SEQ ID NO: 35 |

TABLE 2-continued

Staphylococcus epidermidis

| Protein Name | Amino Acid Length | Signal Sequence | SEQ ID NO |
|---|---|---|---|
| Probable quinol oxidase subunit 2 | 19 | MSKFKSLLLLFGTLILLSG | SEQ ID NO: 36 |
| Probable transglycosylase sceD | 27 | MKKTLVASSLAIGLGVVAGNAG HDAHA | SEQ ID NO: 37 |
| Bifunctional autolysin | 29 | MAKKFNYKLPSMVALTLFGTAF TAHQANA | SEQ ID NO: 38 |
| Extracellular cysteine protease | 30 | MKKKLSYMITIMLAFTLSLALGL FFNSAHA | SEQ ID NO: 39 |
| Membrane protein oxaA 1 | 18 | MHKRLFITLLGFIILLAG | SEQ ID NO: 40 |
| Uncharacterized lipoprotein SE_0144 | 19 | MRYLKRITIYISLLILVSG | SEQ ID NO: 41 |
| N-acetylmuramoyl-L-alanine amidase sle1 | 25 | MQKKYITAIIGTTALSALASTHA QA | SEQ ID NO: 42 |
| Uncharacterized lipoprotein SE_0142 | 22 | MKHSSKIIVFVSFLILTIFIGG | SEQ ID NO: 43 |
| Phosphate-binding protein pstS | 20 | MKKWQLVGTTVLGASVLLGA | SEQ ID NO: 44 |
| Accumulation-associated protein | 52 | MGKRRQGPINKKVDFLPNKLNK YSIRKFTVGTASILLGSTLIFGSSS HEAKA | SEQ ID NO: 45 |
| Staphylococcal secretory antigen ssaA | 26 | MKKIATATIATAGIATFAFAHHD AQA | SEQ ID NO: 46 |
| Serine-aspartate repeat-containing protein F | 45 | MKKRRQGPINKRVDFLSNKVNK YSIRKFTVGTASILVGATLMFGA | SEQ ID NO: 47 |
| Glutamyl endopeptidase | 27 | MKKRFLSICTMTIAALATTTMVN TSYA | SEQ ID NO: 48 |
| Lipase | 35 | MKTRQNKYSIRKFSVGASSILIAA LLFMGGGSAQA | SEQ ID NO: 49 |
| Extracellular elastase | 28 | MKNFSKFALTSIAALTVASPLVN TEVDA | SEQ ID NO: 50 |
| Uncharacterized lipoprotein SE_1947 | 17 | MKKVLASATILSLMLVG | SEQ ID NO: 51 |
| Uncharacterized lipoprotein SE_0186/SE_0187 | 22 | MKYYGKCISYISILILTFFIGG | SEQ ID NO: 52 |
| Uncharacterized lipoprotein SERP2423 | 22 | MKHSSKIIVFVSFLILTIFIGG | SEQ ID NO: 53 |

TABLE 2-continued

Staphylococcus epidermidis

| Protein Name | Amino Acid Length | Signal Sequence | SEQ ID NO |
|---|---|---|---|
| Biofilm PIA synthesis deacetylase icaB | 30 | MKPFKLIFISALMILIMTNATPISHS LNAQA | SEQ ID NO: 54 |
| Probable quinol oxidase subunit 2 | 19 | MSKFKSLLLLFGTLILLSG | SEQ ID NO: 55 |
| Probable transglycosylase sceD | 27 | MKKTLVASSLAIGLGVVAGNAG HDAHA | SEQ ID NO: 56 |
| Uncharacterized lipoprotein SERP2447 | 19 | MHYLKKVTIYISLLILVSG | SEQ ID NO: 57 |
| N-acetylmuramoyl-L-alanine amidase sle1 | 25 | MQKKYITAIIGTTALSALASTHA QA | SEQ ID NO: 58 |
| Uncharacterized lipoprotein SERP2445 | 22 | MKHSKKLLLCISFLLITFFIGG | SEQ ID NO: 59 |
| Staphylococcal secretory antigen ssaA | 26 | MKKIATATIATAGIATFAFAHHD AQA | SEQ ID NO: 60 |
| Uncharacterized lipoprotein SERP2443 | 19 | MRYLKKVTIYISLLILVSG | SEQ ID NO: 61 |
| Glutamyl endopeptidase | 27 | MKKRFLSICTMTIAALATTTMVN TSYA | SEQ ID NO: 62 |
| Phosphate-binding protein pstS | 20 | MKKWQLVGTTVLGASVLLGA | SEQ ID NO: 63 |
| Bifunctional autolysin | 29 | MAKKFNYKLPSMVALTLFGTAF TAHQANA | SEQ ID NO: 64 |
| Extracellular cysteine protease | 30 | MKKKLSYMITIMLAFTLSLALGL FFNSAHA | SEQ ID NO: 65 |
| Membrane protein oxaA 1 | 18 | MHKRLFITLLGFIILLAG | SEQ ID NO: 66 |
| Uncharacterized lipoprotein SERP2422 | 22 | MRYLKKVTIYISLLILTIFIGG | SEQ ID NO: 67 |
| Uncharacterized lipoprotein SERP1959 | 17 | MKKVLASATILSLMLVG | SEQ ID NO: 68 |
| Uncharacterized lipoprotein SERP2453 | 22 | MKHSKKLLLCISFLLITVFISG | SEQ ID NO: 69 |
| Uncharacterized lipoprotein SERP2465 | 22 | MKHSKKLLLCISFLLITFFISG | SEQ ID NO: 70 |
| Probable transglycosylase isaA | 28 | MKKTVIASTLAVSLGIAGYGLSG HEAHA | SEQ ID NO: 71 |

TABLE 2-continued

Staphylococcus epidermidis

| Protein Name | Amino Acid Length | Signal Sequence | SEQ ID NO |
|---|---|---|---|
| Uncharacterized lipoprotein SERP2451 | 22 | MKHSKKLLLCISFLLITIFISG | SEQ ID NO: 72 |
| Probable cell wall amidase lytH | 40 | MKKIDSWLTKHGLKNRLTLVVI VIFIIFLILLFMFVNLSD | SEQ ID NO: 73 |
| Membrane protein oxaA 2 | 19 | MKKKALLPLFLGIMIFLAG | SEQ ID NO: 74 |
| Foldase protein prsA | 20 | MKLMNKIIVPVTASALLLGA | SEQ ID NO: 75 |
| Lipase | 35 | MKTRQNKYSIRKFSVGASSILIAA LLFMGGGSAQA | SEQ ID NO: 76 |

According to some embodiments, the therapeutic LEKTI domain is operably linked to one or more secretion signal sequences derived from endogenous proteins of other bacteria. Non-limiting examples of secretion signal peptides derived from endogenous proteins of various bacteria are set forth in Appendix A.

According to some embodiments, the recombinant LEKTI domain is operably linked to a cell penetration peptide sequence that enhances the ability of the LEKTI domain to pass through a cell membrane. The term "enhance" as used to describe the cell penetration peptide/LEKTI, means that the cell penetration sequence improves the passage of recombinant LEKTI domain through a cell membrane relative to a recombinant LEKTI domain lacking the cell penetration sequence.

Cell penetration peptides: According to some embodiments, one or more cell penetrating peptides are used to mediate delivery of therapeutic proteins in vivo without using cell surface receptors and without causing significant membrane damage. According to some embodiments, one or more cell penetrating peptides are operably linked to therapeutic proteins to facilitate entry into skin cells (e.g. keratinocytes). Non-limiting examples are set forth in Table 3, below:

TABLE 3

| Cell penetrating sequence | SEQ ID NO |
|---|---|
| GRKKRRQRRRPPQ | SEQ ID NO: 77 |
| GWTLNS AGYLLGKINLKALAALAKKIL | SEQ ID NO: 78 |
| KLALKLALKALKAALKLA | SEQ ID NO: 79 |
| WEAKLAKALAKALAKHLAKALAKALKACEA | SEQ ID NO: 80 |
| KETWWETWWTEWSQPKKKRKV | SEQ ID NO: 81 |
| RRRRRRRR | SEQ ID NO: 82 |
| LGTYTQDFNKFHTFPQTAIGVGAP | SEQ ID NO: 83 |
| RQIKWFQNRRMKWKK | SEQ ID NO: 84 |

TABLE 3-continued

| Cell penetrating sequence | SEQ ID NO |
|---|---|
| YGRKKRRQRRR | SEQ ID NO: 85 |
| RGGRLSYSRRRFSTSTGR | SEQ ID NO: 86 |
| RRLSYSRRRF | SEQ ID NO: 87 |
| PIRRRKKLRRLK | SEQ ID NO: 88 |
| RRQRRTSKLMKR | SEQ ID NO: 89 |
| RRRRNRTRRNRRRVR | SEQ ID NO: 90 |
| KMTRAQRRAAARRNRWTAR | SEQ ID NO: 91 |
| TRRQRTRRARRNR | SEQ ID NO: 92 |
| GRKKRRQRRRPPQ | SEQ ID NO: 93 |
| GRRRRRRRRPPQ | SEQ ID NO: 94 |
| GWTLNSAGYLLGKINLKALAALAKKIL | SEQ ID NO: 95 |
| KLALKLALKLALALKLA | SEQ ID NO: 96 |
| MGLGLHLLVLAAALQGAWSQPKKKRKV | SEQ ID NO: 97 |
| GALFLGWLGAAGSTMGAWSQPKKKRKV | SEQ ID NO: 98 |
| GALFLGFLGAAGSTMGAWSQPKKKRKV | SEQ ID NO: 99 |
| GALFLGFLGAAGSTMGAWSQPKSKRKV | SEQ ID NO: 100 |
| KETWWETWWTEWSQPKKKRKV | SEQ ID NO: 101 |
| KETWFETWFTEWSQPKKKRKV | SEQ ID NO: 102 |

According to some embodiments, cell penetrating peptides comprise periodic amino acid sequences. Non-limiting examples of periodic cell penetrating sequences include: Polyarginines, R×n (wherein 4<n<17); Polylysines, K×n (wherein 4<n<17); arginine repeats interspaced with 6-aminocaprotic acid residues (RAca), wherein there are 2 to 6 arginine repeats; arginine repeats interspaced with 4-aminobutyric acid (RAbu), wherein there are 2 to 6 arginine repeats; arginine repeats interspaced with methionine, wherein there are 2 to 6 arginine repeats; arginine repeats interspaced with threonine, wherein there are 2 to 6 arginine repeats; arginine repeats interspaced with serine, wherein there are 2 to 6 arginine repeats; and arginine repeats interspaced with alanine, wherein there are 2 to 6 arginine repeats.

According to some embodiments, the LEKTI domain is operably linker to an RMR domain.

According to some embodiments, expression of the LEKTI domain is controlled by an operon and the amount of LEKTI provided to the mammal's skin is proportional to the availability of an extrinsic factor. For example, in some embodiments the recombinant LEKTI gene may be under the control of a xylose inducible promoter (e.g. xylose repressor (xylR), xylose operator (xylO), xylose isomerase gene (xylA) including the cis-acting catabolite-responsive element (CRE)), and the amount of recombinant LEKTI protein made available to the skin of the mammal controlled by the amount of exogenous xylose available to the recombinant microbe. According to some embodiments, the expression of the LEKTI domain is controlled by a promoter that is constitutively active. According to some embodiments, the expression of the LEKTI domain is controlled by a CmR promoter.

According to some embodiments, the microbe is genetically modified by transfection/transformation with a recombinant DNA plasmid encoding the LEKTI protein domains and one or more antibiotic resistance genes. For example, some embodiments of the recombinant DNA plasmid comprise a kanamycin resistance gene and/or a trimethoprim resistance gene; e.g. dfrA. According to some embodiments, treatment of the skin of the mammal with an antibiotic (for which the recombinant microbe is resistant) may be used to bias the population of commensal microbes toward a larger proportion of LEKTI producing microbes. Other elements that may be present in the recombinant DNA plasmid include, without limitation, a replication protein gene, such as a member of the Rep superfamily of replication proteins. For example, in some embodiments the recombinant DNA plasmid comprises the repF gene.

According to some embodiments, the recombinant DNA plasmid comprises one or more sequences of the pJB38 vector. In some embodiments, the recombinant LEKTI is operably linked to an inducible promoter, ribosome binding site, export signal, and/or cell penetrating peptide in the pJB38 vector. As used herein, the term "pJB38-LEKTI-complete" means a recombinant DNA plasmid construct comprising the pJB38 vector and one or more LEKTI domains. According to some embodiments, the recombinant DNA plasmid comprises the pJB38 vector according to SEQ ID NO: 1542. According to some embodiments, the LEKTI domain is operably linked to the pJB38 vector according to SEQ ID NO: 1542.

According to some embodiments, the recombinant DNA plasmid comprises the pKK30-LEKTI-complete sequence. According to some embodiments, the present disclosure provides a composition for the treatment of a skin disease comprising a microbe comprising the pKK30-LEKTI-complete plasmid construct. According to some such embodiments, the microbe is selected from the group consisting of *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Enterococcus, Pediococcus, Leuconostoc,* or *Oenococcus,* and mixtures thereof.

According to some embodiments, the amount or durations of availability of therapeutic LEKTI protein is controlled by the stability of the vector harboring the LEKTI in a microbe.

For example, the persistence of a recombinant vector may be controlled by one or more elements of a plasmid including those that provide host-beneficial genes, plasmid stability mechanisms, and plasmid co-adaptation. For example, some plasmid may provide for stable replication, active partitioning mechanisms, and mechanisms that insure reliable inheritance of plasmids to daughter cells over generations. (See, e.g., J. C. Baxter, B. E. Funnell, Plasmid partition mechanisms, Microbiol. Spectr., 2 (2014) PLAS-0023-2014 and Nils Hülter et al., An evolutionary perspective on plasmid lifestyle modes, Current Opinion in Microbiology, Volume 38, August 2017, Pages 74-80, each of which are incorporated by herein by reference in its entirety) According to some embodiments, the present invention includes the use of all conventional selection and stability methods known to a person of skill in the art.

According to one aspect, the present disclosure provides a method of treating or ameliorating the effects of a skin disease of a mammal in need thereof comprising, providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin. According to some embodiments, the microbe is adapted to live for a controlled duration on the surface of the mammal's skin and to provide a continuous supply of LEKTI protein domains.

According to another aspect, the present disclosure provides a kit for the treatment or amelioration of the effects of a skin disease of a mammal in need thereof comprising: (1) a composition comprising a microbe that is genetically modified to express one or more LEKTI protein domains, wherein the LEKTI protein domains are effective to penetrate one or more layers of the mammal's skin and effective to inhibit serine protease activity of at least one serine protease in or on the mammal's skin; and (2) reagents for applying the composition to the skin of the mammal. According to some embodiments, the microbes are adapted to live for a controlled duration on the surface of the mammal's skin and to provide a continuous supply of LEKTI protein domains.

In addition to the above components, the subject kits will further include instructions for use of the components and/or practicing the subject methods. These instructions may be present in the subject kits in a variety of forms, one or more of which may be present in the kit. One form in which these instructions may be present is as printed information on a suitable medium or substrate, such as a piece or pieces of paper on which the information is printed, in the packaging of the kit, or in a package insert. Yet another means would be a computer readable medium, such as diskette, or CD, on which the information has been recorded. Further, another means by which the instructions may be present is a website address used via the internet to access the information at a removed site. Any convenient means may be present in the kits.

The components of the kits may be packaged either in aqueous media or in lyophilized form. The kits will generally be packaged to include at least one vial, test tube, flask, bottle, syringe or other container means, into which the described reagents may be placed, and preferably, suitably aliquoted. Where additional components are provided, the kit will also generally contain a second, third or other additional container into which such component may be placed.

The kits of the present disclosure will also typically include a means for containing the reagent containers in close confinement for commercial sale. Such containers may include injection or blow-molded plastic containers into which the desired vials are retained.

Formulations

According to some embodiments the formulation for use according to the present invention can comprise any pharmaceutically effective amount of the recombinant bacteria to produce a therapeutically effective amount of the desired polypeptide or therapeutically effective domain(s) thereof, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of recombinant bacteria, the upper limit of which is about 90.0% by weight of recombinant, bacteria.

According to some embodiments, the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of recombinant bacteria.

According to some embodiments, the topical formulation can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. According to some embodiments, the formulation can include a living cell culture composition and can comprise at least one engineered bacterial strain that produces a therapeutically effective recombinant polypeptide or therapeutically effective domain(s) thereof. This engineered living cell culture composition can deliver the polypeptide directly to the skin for treating or preventing abnormal skin conditions.

Topical formulations include those in which any other active ingredient(s) is (are) dissolved or dispersed in a dermatological vehicle known in the art (e.g. aqueous or nonaqueous gels, ointments, water-in-oil or oil-in-water emulsions). Constituents of such vehicles can comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed can contain one or more components (for example, when the formulation is an aqueous gel, components in addition to water) selected from the following list: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

A film former, when it dries, forms a protective film over the site of application. The film inhibits removal of the active ingredient and keeps it in contact with the site being treated. An example of a film former that is suitable for use in this invention is Flexible Collodion, US P. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emuisifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely-divided.

Lotions will typically contain suspending agents to produce better dispersions as well as compounds useful for localizing and holding the active agent in contact with the skin, e.g., methylcellulose, sodium earhoxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typical 1y aqueous, but also, preferably, contain an alcohol, and, optionally, an oil. Preferred "organic macromolecules," i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter $6$ of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995)(incorporated herein by reference).

Various other additives can be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), $\beta$-tocopherol, $\gamma$-tocopherol, $\delta$-tocopherol, $\epsilon$-tocopherol, $\zeta_1$-tocopherol, $Z^{\char`\^}$-tocopherol, $\eta$-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (Vitamin A), and/or pharmaceutically acceptable salts, esters, amides, or other derivatives thereof. A preferred tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. "Sunscreen drug products for over-the-counter human use" incorporated herein in its entirety.

Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The amounts of these various additives are those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e. glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally involve one or more applications per day on an ongoing basis. One of ordinary skill can readily determine the optimum amount of the formulation to be administered, administration methodologies and repetition rates. In general, it is contemplated that the formulations of the invention will be applied in the range of once or twice weekly up to once or twice daily.

The pharmaceutical compositions of the invention comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22) solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

The following examples are provided to further illustrate the methods of the present invention. These examples are illustrative only and are not intended to limit the scope of the invention in any way.

Example 1

Bacteria

In some embodiments, bacteria of the *Staphylococcus aureus* RN4220 strain may be used in preparation of the vector (Kreiswirth, B N et al. 1983). In some such embodiments, a stock solution of the strain is stored at −20° C. in 50% glycerol in LB or TS broth.

According to some embodiments, bacteria of the *Staphylococcus epidermidis* strain ATCC 12228 or NRRL B-4268 may be used (Zhang, YQ., et ah 2003). In some such embodiments, a stock solution of the strain is stored at −20° C. in 50% glycerol in LB broth or TS broth. Bacteria are cultured in LB broth or TS broth. After 16 hours of incubation, bacteria are harvested by centrifugation and 10-fold concentrated in LB broth or TS broth at $2 \times 10^9$ bacteria/100 ul. A stock preparation of the bacteria is prepared by inoculating 5 mL broth with *S. epidermidis* and grown overnight at 30° C. Then, 3 mL fully grown culture is added to 1 ml 60% glycerol and stored at −80° C.

Expression Vector

According to some embodiments, plasmid construct pKK30-LEKTI-complete may comprise the pKK30 vector with a LEKTI domain insert. According to some embodiments, the LEKTI domain may be operably linked to a SecA secretion signal, a 6×His tag, and/or an RMR cell permeation sequence, with expression under the control of a chloramphenicol-resistance (CmR) promoter sequence (from pDB114E). In some embodiments, the pKK30 vector comprises a dihydrofolate reductase (dfrA) selection gene.

Transformation

According to some embodiments, a vector harboring the LEKTI sequence may be transformed into the *S. epidermidis* strain. The vector harboring the LEKTI sequence may be prepared/transformed comprising the steps of: preparation of competent S. aureus bacterial cells, transformation of S. aureus, isolation of plasmid DNA from S. aureus, preparation of competent S. epidermidis bacterial cells, transformation of S. epidermidis, growth of transformed S. epidermidis bacteria, and storage of transformed S. epidermidis.

In some embodiments, alternative intermediate strains can also be used for transformation and isolation of plasmid DNA in preparation for transformation into S. epidermidis. These strains may include but are not limited to E. coli strains among other bacteria, including those deficient in methylation.

According to some embodiments, S. aureus RN4220 cells may be made electrocompetent by growing 50 ml culture overnight in LB or TS medium at 37° C., then inoculating 100 ml fresh LB or TS medium with 10 ml of overnight culture. When $OD_{600}$ reaches 0.2-0.3, cells are pelleted and resuspended with 1×volume of 4° C. 10% sucrose. This process is repeated 3×, and then the cells are resuspended with 0.1× volume of 4° C. 10% sucrose, pelleted, and resuspended with 1 ml of 10% sucrose.

For transformation of RN4220, 200-500 ug of LEKTI plasmid (e.g. pKK30-LEKTI-complete) may be mixed with electrocompetent cells and transformed using electroporation at room temperature at 2.5 kV using the MicroPulser Electroporator (Bio-Rad, Hercules, Calif.). Transformed cells are plated at 28° C. overnight on selective LB or TB medium, grown overnight in selective LB or TB medium and then used to isolate DNA.

According to some embodiments, electrocompetent S. epidermidis ATCC 12228 or NRRL B-4268 are made using the following methods. First, 50 ml overnight culture of ATCC 12228 or NRRL B-4268 from a −80° C. stock are grown at 37° C. in B2 medium (1.0% tryptone, 2.5% yeast extract, 0.5% glucose, 2.5% NaCl, 0.1% $K_2PO_4$, pH to 7.5). 10 ml of overnight culture is diluted into fresh pre-warmed B2 media and shaken until $OD_{600}$ reaches 0.5-0.6 and then pelleted for 10 min at 4° C. Next, cells are washed with 1, 1/2, 1/20, and 1/50 volumes of cold 10% glycerol, pelleting at 4° C. between washes. The final pellet is resuspended in 700 ul of cold 10% glycerol.

According to some embodiments, electrocompetent ATCC 12228 or NRRL B-4268 are transformed with pKK30-LEKTI-complete, isolated from S. aureus, using electroporation at 2.5 kV, 25 uF, 100Ω. (normal reading is 4.5-5 msec using the Micropulser Electroporator (Bio-Rad, Hercules, Calif.)). Cells are then plated at 28° C. on selective LB or TB medium. In some embodiments, transformation of the bacteria can also be performed via alternative methods of transformation including but not limited to alternative intermediate strains, bacteriophage transduction, and heat shock.

Analysis of Protein Expression

According to some embodiments, transformed cells are fractionated and analyzed via SDS-PAGE electrophoresis and western blotting. Bacterial cells expressing recombinant LEKTI and bacterial control cells are pelleted and lysed with CelLytic B Cell Lysis Reagent (Sigma-Aldrich, St. Louis, Mo.). The supernatant from the induced sample is collected and concentrated. Samples are resuspended in a reduced sample buffer and then electrophoresed on a 4-15% Trisacrylimide gel with Tris-HCL running buffer. Following electrophoresis, the gel is transferred to a PVDF membrane, and sequentially probed with a primary goat monoclonal antibody against LEKTI domains 8-11 or a His tag. A horseradish peroxidase-conjugated donkey anti-goat antibody (sc-2020) is then probed and the secondary antibodies detected through autoradiography (Syngene GeneGnome Bio Imaging System) using enhanced chemiluminescence substrate (SuperSignal West Pico, Thermo Scientific).

Analysis of the supernatant and cell lysate demonstrates the successful expression and secretion of the therapeutic polypeptide upon transformation with a plasmid containing the protein of interest. Detection of protein expression and secretion is also possible using alternative methods and the current example should not be construed as a limitation to the present invention.

Treatment of Human Subjects

According to some embodiments, $1 \times 10^9$ colony forming units (CFU) of S. epidermidis containing recombinant LEKTI can be added to a pharmaceutically acceptable carrier. The foregoing composition is useful for treating or preventing abnormal skin conditions resulting from Netherton Syndrome in a subject in need thereof. The composition can be applied at least once per day, up to for example about 3 to 4 times per day, or as needed or prescribed. In some embodiments, only a single application is required to achieve a therapeutic effect. The composition can be used for as long as needed to ensure treatment of the condition or to continue to prevent the condition. The duration of treatment can vary from about 1 day up to about 10 to 14 days or longer. In certain instances, long term or chronic treatment can be administered.

Example 2

Testing Serine Protease Inhibition Activity of Recombinant LEKTI

According to some embodiments, the protease inhibition activity of recombinant LEKTI is tested for differences achieved when operably linked to various secretion peptides and cell penetration peptides. According to some embodiments, specific combinations of secretion peptides and cell penetration peptides may have unpredictable effects on the protease inhibition function of the LEKTI domains, and therefore may be determined empirically.

In some embodiments, LEKTI domains D8-D11, operably linked to a secretory tag, 6×His tag, and/or cell penetration tag, are cloned into an insect expression vector for large scale production of purified recombinant protein and assessed for inhibitory activity on one or more proteases (e.g. plasmin, cathepsin G, elastase, and trypsin).

Insect Cells and Reagents

The following reagents may be obtained commercially as indicated: Fall Army worm cell line Spodoptera frugiperda (Sf9), low-melting point agarose, cellFECTIN, pFASTBAC1, pCRII-TOPO, Escherichia colicompetent DH10BAC, cabbage looper egg cell line Trichoplusia ni 5B1-4 (High Five), and ultimate serum-free insect medium from Invitrogen (Carlsbad, Calif.); restriction endonucleases from New England Biolabs (Beverly, Mass.); TALON Superflow from Clontech Laboratory (Palo Alto, Calif.); Insect-XPRESS medium and fetal bovine serum from BioWhittaker (Walkersville, Md.); YM10 Centriplus from Millipore Corp. (Bedford, Mass.); precast SDS-PAGE gels, protein assay kit, SEC-250 size column, and prestained markers from Bio-Rad (Hercules, Calif.); BSA from Kabi Pharmacia (Franklin, Ohio); DTT and glycerol from Boehringer Mannheim Biochemicals (Indianapolis, Ind.); and penta-His mAb and six-His tagged protein ladder from QIAGEN Inc. (Valencia, Calif.).

Cloning and Expression of LEKTI D8-D11

6×His tagged LEKTI domains operably linked to various permutations of secretion peptides and cell penetration peptides may be cloned into the pFASTBAC1 vector according to the manufacturers' instructions. Recombinant LEKTI composite viruses are then generated as previously described by Gao, M. et al., (1996) J. Biol. Chem. 271, 27782-27787, which is incorporated herein by reference in its entirety. To test the recombinant LEKTI composite viruses for recombinant LEKTI expression, Sf9 cells may be infected at varying multiplicities of infection with recombinant viruses, and the cell lysate and medium collected every 24-96 h. The presence of histidine-tagged protein may be confirmed by Western blot analysis using penta-His mAb directed against the six-histidine tag as per the manufacturer's recommendations. LEKTI composite viruses that displayed the highest level of expression may be chosen for further experiments and spinner flasks.

The recombinant LEKTI protein may be produced on a large scale by infecting spinner cultures of Sf9 cells (1.6 billion cells) in 10% serum containing Insect-XPRESS medium at a multiplicity of infection of 8 plaque forming units (PFU). Three days after infection, the cell pellet may be harvested and the recombinant LEKTI selectively purified from the cell lysate using a $Co^{2+}$-charged Sepharose affinity column (TALON) followed by SEC-250 size column chromatography, as previously described in Jayakumar, A. et al., (1995) Proc. Natl. Acad. Sci. U.S.A. 92, 8695-8699. Fractions containing homogeneous LEKTI may be pooled and concentrated by ultrafiltration. Protein may be quantified using the Bio-Rad Protein Assay Kit II.

Protease Inhibition Assay Reagents and Protocol

The following enzymes, chromogenic substrates, and reagents may be obtained commercially as indicated: human plasmin, human cathepsin L, human cathepsin S, human trypsin, human cathepsin G, human chymotrypsin, and human neutrophil elastase (HNE) from Athens Research & Technology, Inc. (Athens, Ga.); subtilisin A from Calbiochem-Novabiochem (San Diego, Calif.); papain from Roche Molecular Biochemicals (Indianapolis, Ind.); furin from New England BioLabs; succinyl-Ala-Ala-Pro-Phe-p-nitroanilide (Succ-AAPF-pNA), succinyl-Ala-Ala-Val-pNA (Succ-AAVpNA), andD-Val-Leu-Lys-pNA (VLK-pNA) from Sigma Chemical Co. (St. Louis, Mo.); H-Glu-Gly-Arg-pNA (EGRpNA) and benzyloxycarbonyl-Phe-Arg-pNA (Z-FR-pNA) from Bachem Bioscience, Inc. (King of Prussia, Pa.); and methoxy-Succ-Arg-Pro-Tyr-pNA (MeO-Succ-RPY-pNA) from Chromogenix Instrumentation Laboratory SpA (Milan, Italy). PBS reaction buffer (137 mM NaCl, 27 mM KCl, and 10 mM phosphate buffer (pH 7.4)) may be used with trypsin, plasmin, cathepsin G, HNE, and chymotrypsin. Cathepsin reaction buffer (0.1% CHAPS, 50 mM sodium acetate (pH 5.5), 1 mM EDTA) may be used with cathepsins K, L, and S and papain. A unique reaction buffer may be used with subtilisin A (PBS and 0.1% Tween 20).

Proteinase inhibitory activity may be detected by the ability of recombinant LEKTI to block the cleavage of small, chromogenic peptide substrates as determined by a spectroscopy technique described previously in Schick, C. et al., (1998) Biochemistry 37, 5258-5266, which is incorporated herein by reference in its entirety. Inhibition of proteinase may be assessed after preincubating the enzyme with recombinant LEKTI for 2 min at 25° C. in 100 uL of assay buffer. This mixture may be added to 890 or 880 uL of assay buffer in a 1 mL quartz cuvette. The proteinase activity may be initiated by adding 10-20 uL of the appropriate pNA substrate. The change in absorbance at 405 nm (A405=8.8 $10^{-3}$ $M$ $cm^{-1}$) may be followed for as long as 10 min using a spectrophotometer (Beckman Instruments, Inc., Fullerton, Calif.). The rate changes ($\Delta A4_{405}$/min) of inhibited and control reactions may be determined from velocity plots.

According to some embodiments, different combinations of secretory tag and cell penetration tag may cause differing LEKTI protease activity on each of the tested proteases (e.g. trypsin, plasmin, cathepsin G, HNE, subtilisin A, and chymotrypsin). Furthermore, discrete combinations of secretory tag and cell penetration tag may cause differing LEKTI protease activity among individual proteases.

Example 3

Penetrating Peptide Mediated Delivery

According to some embodiments, various combinations of secretory tag and cell penetration tag may affect the ability of the recombinant LEKTI protein to pass through a cell membrane to a greater or lesser degree. Thus, the various recombinant LEKTI products may be tested in cell culture to assess the effect of the various combinations of secretory tag and cell penetration tag.

According to some embodiments, adherent fibroblastic HS-68, NIH-3T3, 293, Jurkat T, or Cos-7 cell lines may be cultured in Dulbecco's modified Eagle's medium (DMEM) supplemented with 1% (vol/vol) 200 mM glutamine, 1% (vol/vol) antibiotics (streptomycin, 10,000 µg/ml; penicillin, 10,000 IU/ml), and 10% (wt/vol) FBS, at 37° C. in a humidified atmosphere containing 5% CO2. For peptide-mediated delivery of recombinant LEKTI proteins, purified recombinant LEKTI product (as obtained above) may be loaded in DMEM or PBS (500 µl of DMEM containing 0.25 µg of protein) and incubated for 30 min at 37° C. Cells grown to 75% confluency are then overlaid with these recombinant LEKTI protein media. After 30 min incubation at 37° C., 1 ml of fresh DMEM supplemented with 10% FBS is added to the cells, without removing the overlay of recombinant LEKTI protein, and cells are returned to the incubator for another 30 min. Cells are then extensively washed with PBS and examined for recombinant LEKTI protein. Cells could be observed by immunofluorescence by first fixing with 2% formalin (Sigma), permeabilizing, then incubating with primary anti-6xHis tag antibody and secondary antibody according to the manufacturers' instruction. Alternatively cells lysates could be obtained and the presence of His tagged recombinant LEKTI observed via Western blot, as described above.

According to some embodiments, certain combinations of secretory protein and penetrating peptide have differing effects on the ability of the recombinant LEKTI protein's ability to pass through the cell membrane.

Example 4

Figure 3:
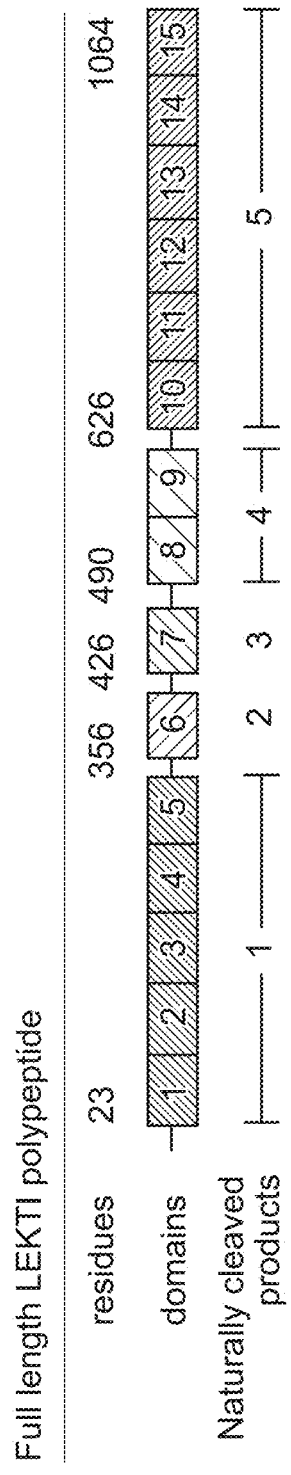
FIG. 3 is a schematic showing the domains of the full length LEKTI polypeptide.

The LEKTI protein requires proteolytic cleavage for activation of its inhibitory function against many proteases. The full length protein is cleaved into domains D1-D5 and D6-D15. The D6-D15 domains are then further cleaved in multiple steps into D6-D9 and D10-D15, →D6 and D7-D9→D7 and D8-D9→D8. A schematic of the full-length LETKI polypeptides, the domains and the naturally cleaved products is shown in FIG. 3. In selecting a particular domain to express, the following criteria of the domain were considered: (1) active on various kallikrein-related peptidases (KLK) such as KLK5 and KLK7; (2) protease resistant; (3) small (not a metabolic burden); (4) contains minimal disulfide bond content. Domain 6 was selected as a LETKI fragment to express. The amino acid sequence of full length LEKTI protein is set forth as SEQ ID NO:103. as well as each of the 15 individual domains below in fasta format:

```
LEKTI amino acid sequence Residues 1-1064
(SEQ ID NO: 103):
MKIATVSVLLPLALCLIQDAASKNEDQEMCHEFQAFMKNGKLFCPQDKKF

FQSLDGIMFINKCATCKMILEKEAKSQKRARHLARAPKATAPTELNCDDF

KKGERDGDFICPDYYEAVCGTDGKTYDNRCALCAENAKTGSQIGVKSEGE

CKSSNPEQDVCSAFRPFVRDGRLGCTRENDPVLGPDGKTHGNKCAMCAEL

FLKEAENAKREGETRIRRNAEKDFCKEYEKQVRNGRLFCTRESDPVRGPD

GRMHGNKCALCAEIFKQRFSEEENSKTDQNLGKAEEKTKVKREIVKLCSQY

QNQAKNGILFCTRENDPIRGPDGKMHGNLCSMCQAYFQAENEEKKKAEAR

ARNKRESGKATSYAELCSEYRKLVRNGKLACTRENDPIQGPDGKVHGNTC

SMCEVFFQAEEEEKKKKEGKSRNKRQSKSTASFEELCSEYRKSRKNGRLF

CTRENDPIQGPDGKMHGNTCSMCEAFFQQEERARAKAKREAAKEICSEFR

DQVRNGTLICTREHNPVRGPDGKMHGNKCAMCASVFKLEEEEKKNDKEEK

GKVEAEKVKREAVQELCSEYRHYVRNGRLPCTRENDPIEGLDGKIHGNTC

SMCEAFFQQEAKEKERAEPRAKVKREAEKETCDEFRRLLQNGKLFCTREN

DPVRGPDGKTHGNKCAMCKAVFQKENEERKRKEEEDQRNAAGHGSSGGGG

GNTQDECAEYREQMKNGRLSCTRESDPVRDADGKSYNNQCTMCKAKLERE

AERKNEYSRSRSNGTGSESGKDTCDEFRSQMKNGKLICTRESDPVRGPDG

KTHGNKCTMCKEKLEREAAEKKKKEDEDRSNTGERSNTGERSNDKEDLCR

EFRSMQRNGKLICTRENNPVRGPYGKMHINKCAMCQSIFDREANERKKKD

EEKSSSKPSNNAKDECSEFRNYIRNNELICPRENDPVHGADGKFYTNKCY

MCRAVFLTEALERAKLQEKPSHVRASQEEDSPDSFSSLDSEMCKDYRVLP

RIGYLCPKDLKPVCGDDGQTYNNPCMLCHENLIRQTNTHIRSTGKCEESS

TPGTTAASMPPSDE
```

LEKTI Domains are set forth below:

```
LEKTI Domain 1
              (residues 23-77; SEQ ID NO: 104)
KNEDQEMCHEFQAFMKNGKLFCPQDKKFFQSLDGIMFINKCATCKMILEK

EAKSQ

LEKTI Domain 2
              (residues 91-153; SEQ ID NO: 105)
APTELNCDDFKKGERDGDFICPDYYEAVCGTDGKTYDNRCALCAENAKTG

SQIGVKSEGECKS

LEKTI Domain 3
              (residues 155-216; SEQ ID NO: 106)
NPEQDVCSAFRPFVRDGRLGCTRENDPVLGPDGKTHGNKCAMCAELFLKE

AENAKREGETRI

LEKTI Domain 4
              (residues 219-285; SEQ ID NO: 107)
NAEKDFCKEYEKQVRNGRLFCTRESDPVRGPDGRMHGNKCALCAEIFKQR

FSEEENSKTDQNLGKAEE

LEKTI_Domain 5
              (residues 291-352; SEQ ID NO: 108)
REIVKLCSQYQNQAKNGILFCTRENDPIRGPDGKMHGNLCSMCQAYFQAE

NEEKKKAEARAR

LEKTI_Domain 6
              (residues 356-423; SEQ ID NO: 109)
ESGKATSYAELCSEYRKLVRNGKLACTRENDPIQGPDGKVHGNTCSMCEV

FFQAEEEEKKKKEGKSRN

LEKTI Domain 7
              (residues_431-489; SEQ ID NO: 110)
ASFEELCSEYRKSRKNGRLFCTRENDPIQGPDGKMHGNTCSMCEAFFQQE

ERARAKAKR

LEKTI Domain 8
              (residues 490-550; SEQ ID NO: 111)
EAAKEICSEFRDQVRNGTLICTREHNPVRGPDGKMHGNKCAMCASVFKLE

EEEKKNDKEEKG

LEKTI Domain 9
              (residues_561_622; SEQ ID NO: 112)
EAVQELCSEYRHYVRNGRLPCTRENDPIEGLDGKIHGNTCSMCEAFFQQE

AKEKERAEPRAK

LEKTI Domain 10
              (residues 626-688; SEQ ID NO: 113)
EAEKETCDEFRRLLQNGKLFCTRENDPVRGPDGKTHGNKCAMCKAVFQKE

NEERKRKEEEDQR

LEKTI Domain 11
              (residues 701-757; SEQ ID NO: 114)
GNTQDECAEYREQMKNGRLSCTRESDPVRDADGKSYNNQCTMCKAKLERE

AERKNEY

LEKTI Domain 12
              (residues 768-830; SEQ ID NO: 115)
ESGKDTCDEFRSQMKNGKLICTRESDPVRGPDGKTHGNKCTMCKEKLERE

AAEKKKKEDEDRS

LEKTI Domain 13
              (residues 843-905; SEQ ID NO: 116)
NDKEDLCREFRSMQRNGKLICTRENNPVRGPYGKMHINKCAMCQSIFDRE

ANERKKKDEEKSS

LEKTI Domain 14
              (residues 910-970; SEQ ID NO: 117)
NNAKDECSEFRNYIRNNELICPRENDPVHGADGKFYTNKCYMCRAVFLTE

ALERAKLQEKPS

LEKTI Domain 15
              (residues 987-1048; SEQ ID NO: 118)
SLDSEMCKDYRVLPRIGYLCPKDLKPVCGDDGQTYNNPCMLCHENLIRQT

NTHIRSTGKCEE
```

LEKTI nucleic acid sequence is set forth below as SEQ ID NO:119.

```
LETKI Full length Nuceic acid sequence
                            (SEQ ID NO: 119)
ATGAAGATAGCCACAGTGTCAGTGCTTCTGCCCTTGGCTCTTTGCCTCAT

ACAAGATGCTGCCAGTAAGAATGAAGATCAGGAAATGTGCCATGAATTTC

AGGCATTTATGAAAAATGGAAAACTGTTCTGTCCCCAGGATAAGAAATTT

TTTCAAAGTCTTGATGGAATAATGTTCATCAATAAAATGTGCCACGTGCAA
```

-continued

```
AATGATACTGGAAAAAGAAGCAAAATCACAGAAGAGGGCCAGGCATTTAG

CAAGAGCTCCCAAGGCTACTGCCCCAACAGAGCTGAATTGTGATGATTTT

AAAAAAGGAGAAAGAGATGGGGATTTTATCTGTCCTGATTATTATGAAGC

TGTTTGTGGCACAGATGGGAAAACATATGACAACAGATGTGCACTGTGTG

CTGAGAATGCGAAACCGGGTCCCAAATTGGTGTAAAAAGTGAAGGGGAA

TGTAAGAGCAGTAATCCAGAGCAGGATGTATGCAGTGCTTTTCGGCCCTT

TGTTAGAGATGGAAGACTTGGATGCACAAGGGAAAATGATCCTGTTCTTG

GTCCTGATGGGAAGACGCATGGCAATAAGTGTGCAATGTGTGCTGAGCTG

TTTTTAAAAGAAGCTGAAAATGCCAAGCGAGAGGGTGAAACTAGAATTCG

ACGAAATGCTGAAAAGGATTTTTGCAAGGAATATGAAAAACAAGTGAGAA

ATGGAAGGCTTTTTGTACACGGGAGAGTGATCCAGTCCGTGGCCCTGAC

GGCAGGATGCATGGCAACAAATGTGCCCTGTGTGCTGAAATTTTCAAGCA

GCGTTTTTCAGAGGAAAACAGTAAAACAGATCAAAATTTGGGAAAGCTG

AAGAAAAAACTAAAGTTAAAAGAGAAATTGTGAAACTCTGCAGTCAATAT

CAAAATCAGGCAAAGAATGGAATACTTTTCTGTACCAGAGAAAATGACCC

TATTCGTGGTCCAGATGGGAAAATGCATGGCAACTTGTGTTCCATGTGTC

AAGCCTACTTCCAAGCAGAAAATGAAGAAAAGAAAAAGGCTGAAGCACGA

GCTAGAAACAAAAGAGAATCTGGAAAAGCAACCTCATATGCAGAGCTTTG

CAGTGAATATCGAAAGCTTGTGAGGAACGGAAAACTTGCTTGCACCAGAG

AGAACGATCCTATCCAGGGCCCAGATGGGAAAGTGCATGGCAACACCTGC

TCCATGTGTGAGGTCTTCTTCCAAGCAGAAGAAGAAGAAAAGAAAAAGAA

GGAAGGTAAATCAAGAAACAAAAGACAATCTAAGAGTACAGCTTCCTTTG

AGGAGTTGTGTAGTGAATACCGCAAATCCAGGAAAAACGGACGGCTTTTT

TGCACCAGAGAGAATGACCCCATCCAGGGCCCAGATGGAAAAATGCATGG

CAACACCTGCTCCATGTGTGAGGCCTTCTTTCAACAAGAAGAAAGAGCAA

GAGCAAAGGCTAAAGAGAAGCTGCAAAGGAAATCTGCAGTGAATTTCGG

GACCAAGTGAGGAATGGAACACTTATATGCACCAGGGAGCATAATCCTGT

CCGTGGCCCAGATGGCAAAATGCATGGAAACAAGTGTGCCATGTGTGCCA

GTGTGTTCAAACTTGAAGAAGAAGAAGAAAAATGATAAAGAAGAAAAA

GGGAAAGTCGAGGCTGAAAAAGTTAAGAGAGAAGCAGTTCAGGAGCTGTG

CAGTGAATATCGTCATTATGTGAGGAATGGACGACTCCCCTGTACCAGAG

AGAATGATCCTATTGAGGGTCTAGATGGGAAAATCCACGGCAACACCTGC

TCCATGTGTGAAGCCTTCTTCCAGCAAGAAGCAAAAGAAAAAGAAAGAGC

TGAACCCAGAGCAAAAGTCAAAAGAGAAGCTGAAAAGGAGACATGCGATG

AATTTCGGAGACTTTTGCAAAATGGAAAACTTTTCTGCACAAGAGAAAAT

GATCCTGTGCGTGGCCCAGATGGCAAGACCCATGGCAACAAGTGTGCCAT

GTGTAAGGCAGTCTTCCAGAAAGAAAATGAGGAAAGAAAGAGGAAAGAAG

AGGAAGATCAGAGAAATGCTGCAGGACATGGTTCCAGTGGTGGTGGAGGA

GGAAACACTCAGGACGAATGTGCTGAGTATCGGGAACAAATGAAAAATGG

AAGACTCAGCTGTACTCGGGAGAGTGATCCTGTACGTGATGCTGATGGCA

AATCGTACAACAATCAGTGTACCATGTGTAAAGCAAAATTGGAAAGAGAA

GCAGAGAGAAAAAATGAGTATTCTCGCTCCAGATCAAATGGGACTGGATC

AGAATCAGGGAAGGATACATGTGATGAGTTTAGAAGCCAAATGAAAAATG

GAAAACTCATCTGCACTCGAGAAAGTGACCCTGTCCGGGGTCCAGATGGC

AAGACACATGGCAATAAGTGTACTATGTGTAAGGAAAAACTGGAAAGGGA

AGCAGCTGAAAAAAAAAGAAAGAGGATGAAGACAGGAGCAATACAGGAG

AAAGGAGCAATACAGGAGAAAGGAGCAATGACAAAGAGGATCTGTGTCGT

GAATTTCGAAGCATGCAGAGAAATGGAAAGCTTATCTGCACCAGAGAAAA

TAACCCTGTTCGAGGCCCATATGGCAAGATGCACATCAATAAATGTGCTA

TGTGTCAGAGCATCTTTGATCGAGAAGCTAATGAAAGAAAAAGAAAGAT

GAAGAGAAATCAAGTAGCAAGCCCTCAAATAATGCAAAGGATGAGTGCAG

TGAATTTCGAAACTATATAAGGAACAATGAACTCATCTGCCCTAGAGAGA

ATGACCCAGTGCACGGTGCTGATGGAAAGTTCTATACAAACAAGTGCTAC

ATGTGCAGAGCTGTCTTTCTAACAGAAGCTTTGGAAAGGGCAAAGCTTCA

AGAAAAGCCATCCCATGTTAGAGCTTCTCAAGAGGAAGACAGCCCAGACT

CTTTCAGTTCTCTGGATTCTGAGATGTGCAAAGACTACCGAGTATTGCCC

AGGATAGGTTATCTTTGTCCAAAGGATTTAAAGCCTGTCTGTGGTGACGA

TGGCCAAACCTACAACAATCCTTGCATGCTCTGTCATGAAAACCTGATAC

GCCAAACAAATACACACATCCGCAGTACAGGGAAGTGTGAGGAGAGCAGC

ACCCCAGGAACCACCGCAGCCAGCATGCCCCCGTCTGACGAA
```

Solubility in *E. coli* BL21 (De3)

Prokaryotes produce soluble and inclusion body bound protein. Solubility is influenced by temperature, protein charge and protein structure and size. Insoluble inclusion bound protein is often misfolded, is typically inactive, and is isolated in very pure and insoluble inclusion bodies. Inclusion bound protein is isolated and re-folded in vitro, and then purified. Soluble protein is in a folded structure, is often functional and exists in the cytoplasm with the rest of proteome.

Figure 4:
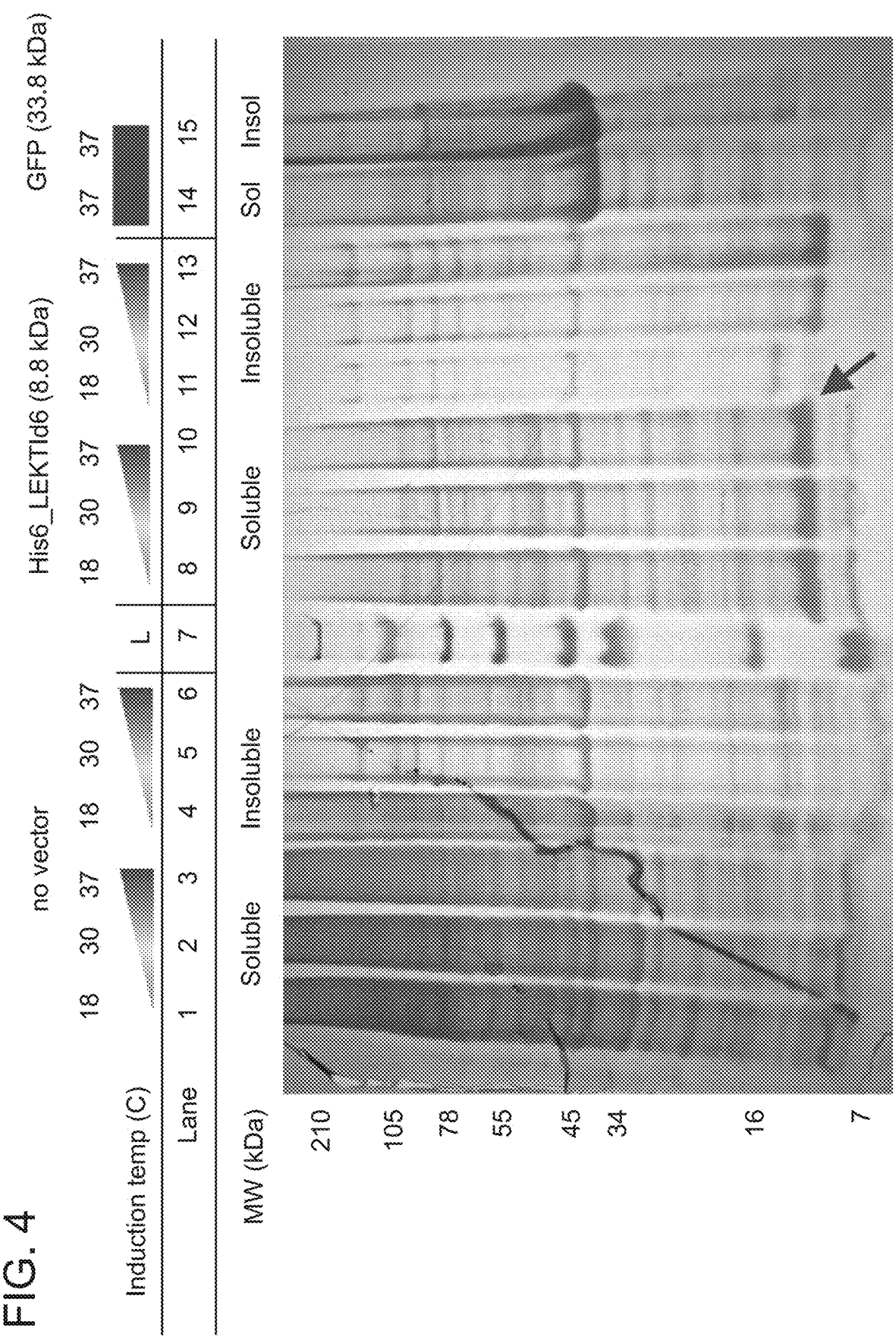
FIG. 4 shows SDS-PAGE results demonstrating that LEKTId6 is highly soluble in *E. coli* BL21 (De3).

A first set of experiments were performed to determine if domain 6 was produced reliably in *E Coli*. Soluble protein was isolated by affinity purification and buffer exchange, and then purified. Solubility test assays were used to determine the distribution between inclusion body protein and soluble protein fraction. Briefly, domain 6 protein expressing cells (*E. coli* BL21 (De3)) were lysed with aqueous buffer. High speed centrifugation and inclusion body purification were used to isolate the soluble fraction and inclusion body fraction. The isolated fractions were subjected to sodium dodecylsulphate polyacrylamide gel electrophoresis (SDS-PAGE). FIG. 4 shows results from SDS-PAGE demonstrating that LEKTId6 (8.8 kDa) was highly soluble in *E. coli* BL21 (De3). *E. coli* GFP (33.8 kDa) was used as a positive control, and no vector was used as a negative control. Experiments were performed at three different induction temperatures: 18, 30 and 37° C. As shown in FIG. 4, a band at 8.8 kDa was detected in the soluble fraction of the His6_LEKTId6 experimental group. The arrow indicates the band at 8.8 kDa.

Figure 5:
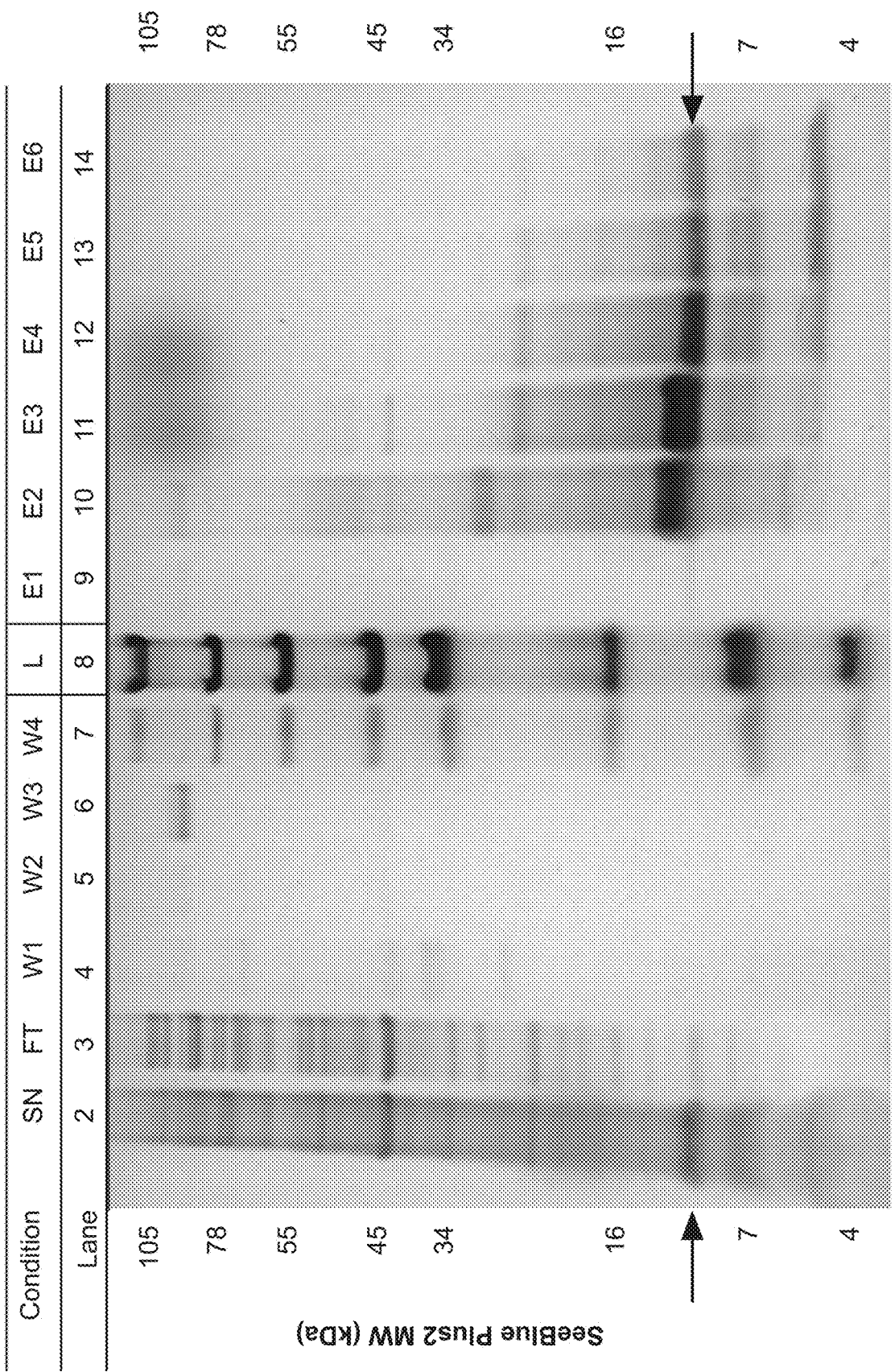
FIG. 5 shows SDS-PAGE results demonstrating successful affinity purification for H6-LEKTId6 (8.8 kDa).
Figure 6:
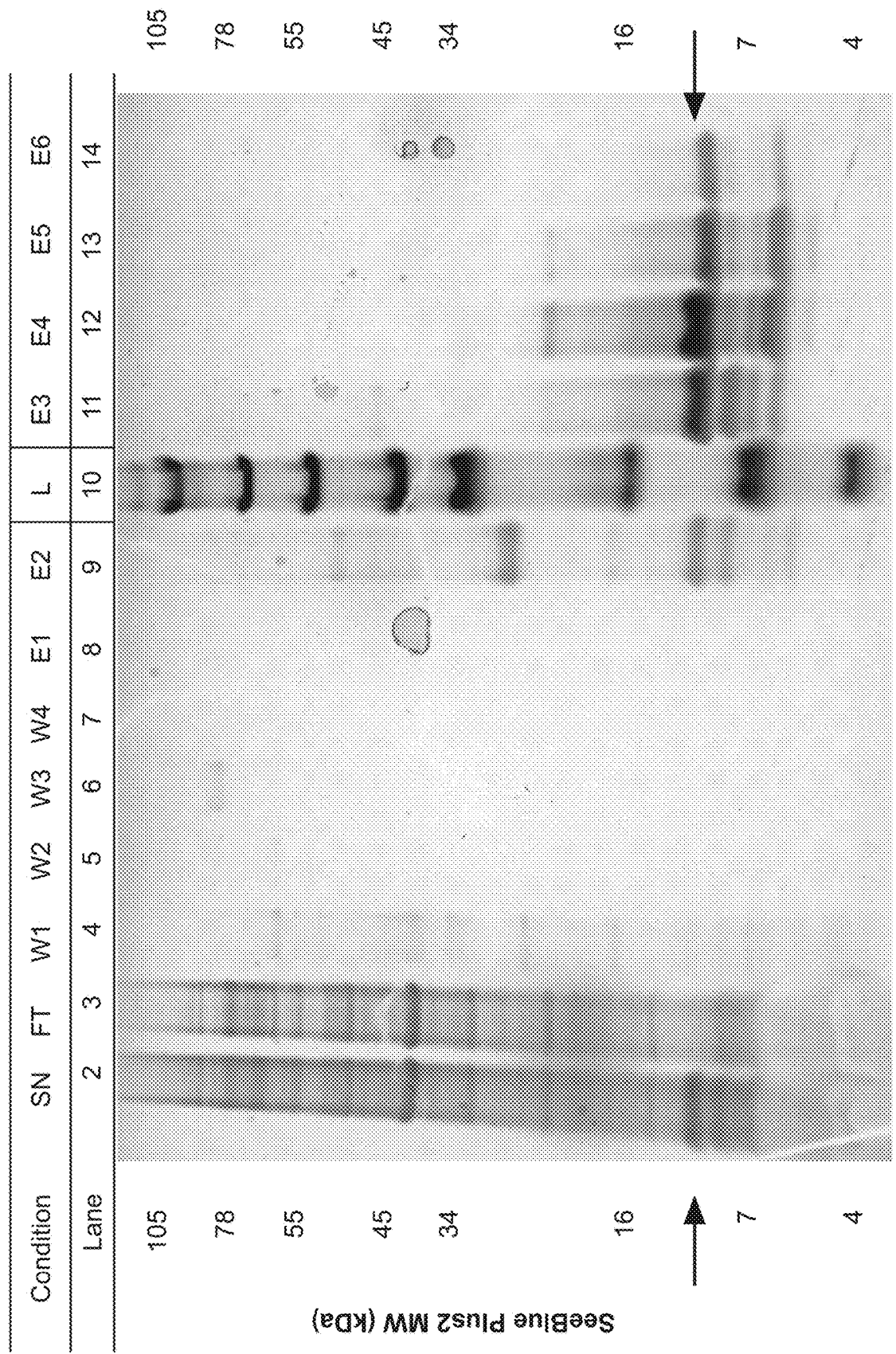
FIG. 6 shows SDS-PAGE results demonstrating LEKTId6-H6 (8.8 kDa) is potentially N-terminally truncated.

FIG. 5 shows results from SDS-PAGE demonstrating that affinity purification was successfully carried out for H6-LEKTId6 (8.8 kDa). The arrows indicate the band at 8.8 kDa. FIG. 6 shows that LEKTId6-H6 (8.8 kDa) may be N-terminally truncated. In both FIG. 5 and FIG. 6, the following abbreviations were used to for experimental groups:

SN=clarified cell lysate (supernatant)
FT=non-Ni2+ bound protein (flow-through)
W1-4=eluents from a series of washes (1-4). Note some contamination from the neighboring ladder in W4.
L=SDS-PAGE protein ladder (SeeBlue Plus2, ThermoFisher Scientific)
E1-6=eluents from the column after imidazole treatment (i.e. the resulting affinity-purified protein). As the column is treated, different eluent fractions (1-6) were collected.

Example 5

The capacity of purified recombinant LEKTI Domain 6 (LETKId6) fragments to function in vitro as a serine protease inhibitor was assessed.

First, the ability of recombinantly produced LEKTId6 to inhibit trypsin in vitro was determined. Enzyme activity was measured using BApNA (Nα-benzoyl-l-arginine-p-nitroanilide) as substrate specific for trypsin. FIG. 7A shows a schematic overview of the assay. The assay was carried out by mixing 80 uL of LEKTId6 at concentrations (0.25, 2.5, 25 uM) with 20 uL of trypsin (35 ug/mL) and 100 uL of 2× trypsin assay buffer (100 mM Tris-HCl, pH 8.0, 300 mM NaCl, 100 mM CaCl2, 0.02% Triton-X-100, 500 uM L-BAPNA). In the reaction mixture, components were at final concentrations of of LEKTId6 (0.1, 1, 10 uM); trypsin (3.5 ug/mL), assay buffer (50 mM Tris-HCl, pH 8.0, 150 mM NaCl, 50 mM CaCl2, 0.01% Triton-X-100); and L-BAPNA (250 uM). The reaction was allowed to proceed for 15 min at 37° C. The tryspin inhibitor leupeptin was used as a positive control. The formation of product was measured at 405 nm with a microplate reader. A blank control was used. Trypsin activity was defined as the rate of change in the absorbance at 405 nm (an indicator of L-BAPNA cleavage) per minute under the established conditions. As shown in FIG. 7, LEKTI Domain 6 inhibited trypsin activity in vitro.

Next, the effect of LEKTI Domain 6 (ct His6 tag) on trypsin inhibition was determined and compared to the effects of LEKTI domain 10-15 on trypsin inhibition. A trypsin inhibition assay was performed as described above, where enzyme activity was measured using L-BAPNA (Nα-benzoyl-l-arginine-p-nitroanilide) as substrate specific for trypsin. FIG. 8 shows a schematic overview of the assay. LETKId6 (10, 30, 100, 1000 nm) or LEKTI domain 10-15 (10, 30, 100 nm) were mixed with with L-BAPNA (final concentration 250 uM) for 10 min at 25° C. The tryspin inhibitor leupeptin was used as a positive control. The ability of recombinantly produced LEKTId6 to inhibit kallikreins 7 and 5 (KRK7 and KRK5) in vitro was determined. Briefly, proteinases KLK7 and KLK5 were incubated with increased concentrations of LEKTId6 for 5 min at 25° C. before addition of their optimal peptide substrates, which was Suc-Arg-Pro-Tyr-p-Nitro-Anilide for KLK7 and D-Ile-Pro-Arg-p-Nitro-Anilide for KLK5. The formation of product was measured at 405 nm with a microplate reader. A blank control was used. Schematic overviews of the KLK7 assay and the KLK5 assay are shown in FIGS. 9A and 10A, respectively. For KLK7, increasing concentrations of LEKTId6 (10, 30, 100, 300, 1000 nm) and increasing concentrations of LEKTId10-15 (10, 30, 100 nm) were used. The tryspin inhibitor leupeptin was used as a negative control. For KLK5, increasing concentrations of LEKTId6 (10, 30, 100, 300, 1000 nm) were used. As shown in FIG. 9B, recombinantly produced LEKTI Domain 6 inhibits KLK7 in vitro about as well as LEKTI domains 10-15. As shown in FIG. 10B, recombinantly produced LEKTId6 inhibits KLK5 in vitro at nanomolar concentrations. While, high concentrations of LETKId6 were shown to be stimulatory, without being bound by theory, this may be due to a buffer component of the assay, particularly leftover imidazole that remained in the LEKTId6 sample after affinity purification.

Example 6

Efficacy of therapeutic LETKId6 *S. epidermidis* strains will be evaluated in a condition Netherton's mouse model. Briefly, we will validate the absence of LEKTI in the skin of CRISPR created Netherton's syndrome mice (conditional SPINK5−/−) after induction of Cre recombination at 1, 2, and 4 weeks. Mice with a validated Netherton's syndrome phenotype will be treated with topical application of recombinant LEKTI to resolve skin conditions in the Spink5 conditional mutant. The rationale for first using purified LEKTI is to avoid dependency on the construction of *S. epidermidis* strains such that we can rapidly demonstrate the efficacy of topical application in vivo. Second, we will evaluate the ability of *S. epidermidis*—purified or LEKTI to demonstrate the value of probiotic colonization for sustained remediation. As controls, we will topically colonize the same mice pre-Cre-induction of the SPINK5 conditional mutation. To assess the effect of LETKId6 in the mouse model, we will perform longitudinal assays (1×/week) where possible and endpoint assays (3 weeks post-colonization) to test if application of therapeutic *S. epidermidis* will (1) produce detectable amounts of LEKTI in vivo, as measured by immunohistochemical analysis of skin (endpoint), (2) reduce skin disease severity as measured by DASI (longitudinal and endpoint), (3) improve TEWL (longitudinal) and permeability scores (endpoint), (4) ameliorate skin morphology, as measured by histological analysis (endpoint), and (5) result in changes in proteolytic activity, as measured using colorimetric assays that target KLK5 and KLK7 (endpoint).

INCORPORATION BY REFERENCE

The entire disclosure of each of the patent documents, including patent application documents, scientific articles, governmental reports, websites, and other references referred to herein is incorporated by reference herein in its entirety for all purposes. In case of a conflict in terminology, the present specification controls. All sequence listings, or Seq. ID. Numbers, disclosed herein are incorporated herein in their entirety.

The following references, to the extent that they provide exemplary procedural or other details supplementary to those set forth herein, are specifically incorporated herein by reference.

Armengot-Carbo, M. et al. (2014) "The role of filaggrin in the skin barrier and disease development." Actas Dermosifiliogr March; 106 (2):86-95.
Brachkova, M. I., P. Marques, J. Rocha, B. Sepodes, M. A. Duarte and J. F. Pinto (2011). "Alginate films containing *Lactobacillus plantarum* as wound dressing for prevention of burn infection." J Hosp Infect 79(4): 375-377.
Brown, S J., & McLean, W H. (2012) J. Invest. Dermatol. 132, 751-62
Chen, Y E., & Tsao, H. (2013) J. Am. Acad. Dermatol. 69, 143-155

Cheung A L, et al. (2004) "Regulation of virulence determinants in vitro and in vivo in *Staphylococcus aureus*." FEMS Immunological Medical Microbiology 40(1): 1-9

"DNA Recombination." Methods in Molecular Biology 745 (XIV): 1-565.

Gross, et al, WO 94/00098 assigned to Lancaster Group AG

Gross, et al, WO 94/00109 assigned to Lancaster Group AG

Gueniche, A., P. Bastien, J. M. Ovigne, M. Kermici, G. Courchay, V. Chevalier, L. Breton and I. Castiel-Higounenc (2010). "*Bifidobacterium longum* lysate, a new ingredient for reactive skin." Exp Dermatol 19(8): 1-8.

Jeong J G et al. (2011). A Tat-grafted anti-nucleic acid antibody acquires nuclear-localization property and a preference for TAR RNA. Biochem Biophys Res Commun. March 18; 406(3):403-7.

Kreiswirth, B N., et al. (1983). The toxic shock syndrome exotoxin structural gene is not detectably transmitted by a prophage. Nature 305:709-712.

Lauderdale, et al. (2010). Biofilm dispersal of community-associated methicillin-resistant *Staphylococcus aureus* on orthopedic implant material. J. Orthop. Research. 28:55-61

Lee, S H., Jeong, S K. and Ahn, S K. (2006). "An update of the defensive barrier function of skin." Yonsei Med J 47(3): 293-306.

Lin, Y T., Wang, C T., and Chiang, B L. (2007). "Role of bacterial pathogens in atopic dermatitis." Clin Rev Allergy Immunol 33(3): 167-177.

Ma, J., et al.(2014) Cell-penetrating peptides mediated protein cross-membrane delivery and its use in bacterial vector vaccine. Fish & Shellfish Immunology 39 8-16

McAleer, M A., & Irvine, A D. (2013) J. Allergy Clin. Immunol. 131, 280-91.

Mitsudo K. et al., (2003) "Inhibition of Serine Proteinases Plasmin, Trypsin, Subtilisin A, Cathepsin G, and Elastase by LEKTI: A Kinetic Analysis", Biochemistry, 42, 3874-3881

Monk, I., et al. (2012) Direct transformation to manipulate genetically *Staphylococcus aureus* and *Staphylococcus epidermidis*. mBio.

Muizzuddin, N., Maher, W., Sullivan, M., Schnittger, S., and Mammone, T. (2012). "Physiological effect of a probiotic on skin." J Cosmet Sci 63(6): 385-395.

Nakanishi, N., T. Oshida, S. Yano, K. Takeda, T. Yamaguchi and Y. Ito (1986).

"Construction and characterization of new cloning vectors derived from *Streptomyces griseobrunneus* plasmid pBT1 and containing amikacin and sulfomycin resistance genes." Plasmid 15(3): 217-229.

Nakatsuji, T. and R. L. Gallo (2014). "Dermatological therapy by topical application of non-pathogenic bacteria." J Invest Dermatol 134(1): 11-14.

Oehike J et al. (1998).Cellular uptake of an alpha-helical amphipathic model peptide with the potential to deliver polar compounds into the cell interior non-endocytically. Biochim Biophys Acta. November 11; 1414(1-2): 127-39.

Ostenson C G et al. (1997).Galparan: a powerful insulin-releasing chimeric peptide acting at a novel site. Endocrinology. August; 138(8):3308-13.

Otsuka, A., et al. (2014) J. Allergy Clin. Immunol. 133, 139-46.e1-10 (2014).

Peral, M. C, M. A. Martinez and J. C. Valdez (2009). "Bacteriotherapy with *Lactobacillus plantarum* in burns." Int Wound J 6(1): 73-81.

Peral, M. C, M. M. Rachid, N. M. Gobbato, M. A. Huaman Martinez and J. C. Valdez (2010). "Interleukin-8 production by polymorphonuclear leukocytes from patients with chronic infected leg ulcers treated with *Lactobacillus plantarum*." Clin Microbiol Infect 16(3): 281-286

Powers, M E., et al. (2011). J Bacteriol, 193:340-348

Proksch, E., J. M. Brandner and J. M. Jensen (2008). "The skin: an indispensable barrier." Exp Dermatol 17(12): 1063-1072

Remington: The Science and Practice of Pharmacy, 19th edition. Easton, Pa.: Mack Publishing Co., 1995

Sambrook J, et al. (1989). Molecular Cloning: A Laboratory Manual.Cold Spring Harbor Laboratory Press, New York.

Sambrook, J F., and Russell, D W., ed. (2001). Molecular Cloning: A Laboratory Manual, 3rd ed., Vols 1, 2 and 3. Cold Spring Harbor Laboratory Press Simonen, M. and I. Palva (1993). "Protein secretion in *Bacillus* species." Microbiol Rev 57(1): 109-137

Smith, E W., & Maibach, H I., (1995) Percutaneous Penetration Enhancers, CRC Press ISBN 9780849321528

Stout, T E., et al.(2014)/Invest Dermatol. 134, 423-9

The Science and Practice of Pharmacy (1995), 19th Ed. Easton, Pa.: Mack Publishing Co.

Volz, T., Y. Skabytska, E. Guenova, K. M. Chen, J. S. Frick, C. J. Kirschning, S. Kaesler, M. Rocken and T. Biedermann (2014). "Nonpathogenic bacteria alleviating atopic dermatitis inflammation induce IL-10-producing dendritic cells and regulatory Tr1 cells." J Invest Dermatol 134(1): 96-104

Webb, T R., & Hsu, CPS. U.S. Pat. No. 4,659,774 assigned to American Hoechst Corporation Wyman T B, et al. (1997) Design, synthesis, and characterization of a cationic peptide that binds to nucleic acids and permeabilizes bilayers. Biochemistry. March 11; 36(10): 3008-17

Zhang, Y Q., et al. (2003). Genome-based analysis of virulence genes in a non-biofilm-forming *Staphylococcus epidermidis* strain (ATCC12228). Molecular Microbiology 49(6), 1577-1593

Although illustrative embodiments of the present invention have been described herein, it should be understood that the invention is not limited to those described, and that various other changes or modifications may be made by one skilled in the art without departing from the scope or spirit of the invention.

What is claimed is:

1. A composition for the treatment of skin disease comprising a microbe comprising pJB38-LEKTI domain 6-complete plasmid construct.

2. The composition of claim 1, wherein the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof.

3. A composition comprising pJB38-LEKTI domain 6-complete plasmid construct.

4. The composition according to claim 3, wherein the pJB38-LEKTI-complete plasmid construct is expressed in a microbe selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof.

5. A recombinant microorganism capable of secreting a LEKTI polypeptide, wherein the recombinant microorganism comprises an expression vector comprising a first coding sequence comprising a gene capable of expressing the LEKTI polypeptide and a second coding sequence comprising a gene capable of expressing a cell penetrating peptide, wherein the LEKTI polypeptide comprises LEKTI domain 6.

6. The recombinant microorganism of claim 5, wherein LEKTI domain 6 comprises SEQ ID NO:109.

7. A recombinant microorganism capable of secreting a LEKTI polypeptide, wherein the recombinant microorganism comprises an expression vector comprising a first coding sequence comprising a gene capable of expressing the LEKTI polypeptide and a second coding sequence comprising a gene capable of expressing a cell penetrating peptide, wherein the LEKTI polypeptide comprises LEKTI domains 8-11.

8. A composition for the treatment of skin disease comprising a microbe comprising pJB38-LEKTI domain 8-11-complete plasmid construct.

* * * * *